United States Patent
Shane et al.

(10) Patent No.: US 10,398,795 B2
(45) Date of Patent: Sep. 3, 2019

(54) DECONTAMINATION DEVICE AND METHOD USING ULTRASONIC CAVITATION

(71) Applicant: TOMI Environmental Solutions, Inc., Fredrick, MD (US)

(72) Inventors: Halden Stuart Shane, Beverly Hills, CA (US); Johnny Sullivan Cato, Lynwood, CA (US); Charles Liu, Belle Mead, NJ (US)

(73) Assignee: TOMI ENVIRONMENTAL SOLUTIONS, INC., Frederick, MD (US)

( * ) Notice: Subject to any disclaimer, the term of this patent is extended or adjusted under 35 U.S.C. 154(b) by 0 days.

(21) Appl. No.: 15/858,446

(22) Filed: Dec. 29, 2017

(65) Prior Publication Data
US 2019/0201564 A1    Jul. 4, 2019

(51) Int. Cl.
*A61L 2/14*    (2006.01)
*A61L 2/10*    (2006.01)
*A61L 2/00*    (2006.01)

(52) U.S. Cl.
CPC ............... *A61L 2/14* (2013.01); *A61L 2/0011* (2013.01); *A61L 2/10* (2013.01); *A61L 2202/11* (2013.01); *A61L 2202/24* (2013.01)

(58) Field of Classification Search
CPC ........................................................ A61L 2/14
See application file for complete search history.

(56) References Cited

U.S. PATENT DOCUMENTS

| | | | | |
|---|---|---|---|---|
| 5,217,165 | A * | 6/1993 | Takahashi | B05B 17/0615 239/102.2 |
| 5,902,552 | A * | 5/1999 | Brickley | A61L 2/10 422/121 |
| 6,656,424 | B1 * | 12/2003 | Deal | A61L 2/10 250/455.11 |
| 6,706,243 | B1 | 3/2004 | Sias et al. | |
| 2003/0035754 | A1 | 2/2003 | Sias et al. | |
| 2007/0210186 | A1 * | 9/2007 | Fenton | A62C 5/002 239/422 |
| 2007/0224080 | A1 | 9/2007 | Sparks et al. | |
| 2011/0081273 | A1 * | 4/2011 | Sunderland | A61L 9/046 422/3 |
| 2016/0298857 | A1 * | 10/2016 | Weng | F24C 15/2035 |

OTHER PUBLICATIONS

Paxton. H., "Use of Novel Approaches to Reduce Clostridium Difficile in an Inner City Hospital", Mar. 20, 2017, p. 4, InfectionControl. tips.
International Search Report and the Written Opinion of International application No. PCT/US2017/069056 dated Mar. 8, 2018.

* cited by examiner

*Primary Examiner* — Donald R Spamer
(74) *Attorney, Agent, or Firm* — Ping Wang; Morris, Manning & Martin, LLP

(57) ABSTRACT

A method and apparatus for decontaminating substantially enclosed environments by using ultrasonic cavitation of a cleaning fluid to produce a low pressure, low air flow mist that can be activated by a nonthermal plasma actuator to create a cloud of activated hydroxyl species with the capacity to decontaminate articles, open surfaces or substantially enclosed spaces of pathogens, including bacteria, and other pathogenic microorganisms. An automated system and related non-transitory computer medium are also disclosed.

11 Claims, 10 Drawing Sheets

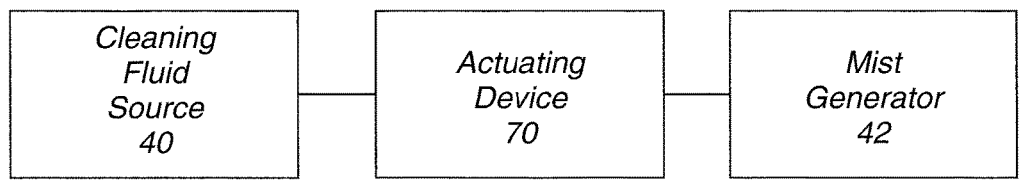
FIG. 10A
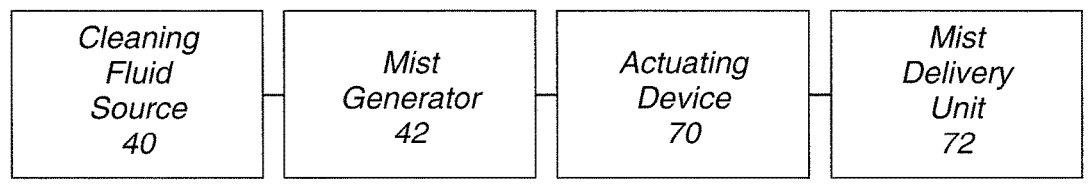
FIG. 10B
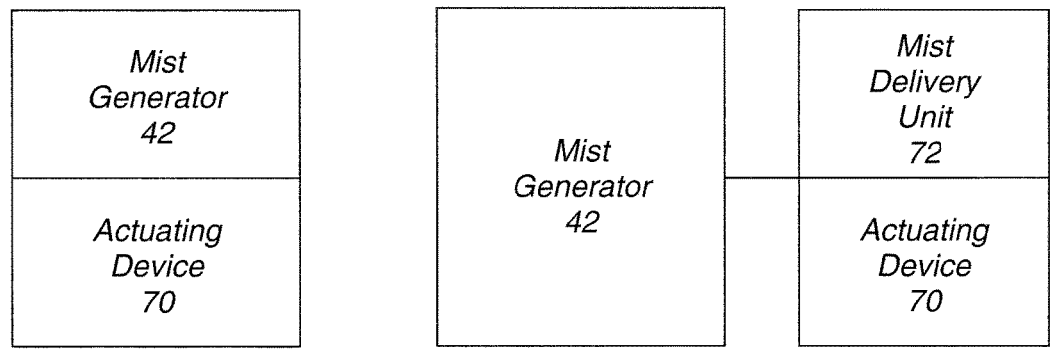
FIG. 10C     FIG. 10D

DECONTAMINATION DEVICE AND METHOD USING ULTRASONIC CAVITATION

FIELD

The present application relates generally to an apparatus and method for decontaminating articles, enclosed spaces, and unenclosed spaces and, more particularly, to microbiological decontamination of such locations.

BACKGROUND

Microbiological species are widely distributed in our environment. Most microbiological species are of little concern, because they do not damage other living organisms. However, other microbiological species may infect man or animals and cause them harm. The removing or rendering ineffective of injurious microbiological organisms has long been of interest. Drugs and medical devices are sterilized and packaged in sterile containers. Medical environments such as operating rooms, wards, and examination rooms are decontaminated by various cleaning procedures so that injurious microbiological organisms cannot spread from one patient to another.

Many available technologies for controlling microbiological organisms are of limited value in the public health circumstances of biological warfare and bioterrorism. Furthermore, current technologies addressing these instances are limited in their effectiveness in tightly enclosed environments. A new approach is needed that is more readily usable in tightly enclosed environments, as well as retaining the ability for use on open surfaces in large spaces, with enhanced kill, and simpler maintenance of machinery. The present invention fulfills this need, and further provides related advantages.

SUMMARY

An aspect of the application is directed to a method for decontaminating an article, surface, or substantially enclosed space, comprising the steps of: shearing a cleaning fluid into a mist comprising aerosol droplets accumulating in a top chamber portion of a substantially closed chamber comprising a funnel shaped top chamber portion, a bottom chamber portion, a side chamber portion and an interior chamber portion, wherein the cleaning fluid is sheared by ultrasonic cavitation; subjecting the mist to a nonthermal plasma actuator to form plasma activated ionic particles; and contacting the article, surface, or substantially enclosed space to the plasma activated ionic particles.

One other aspect of the application is directed to a method for decontaminating an article or substantially enclosed space, comprising the steps of: shearing a cleaning fluid into a mist comprising aerosol droplets by cavitating the cleaning fluid using an ultrasonic cavitator submerged in a substantially closed chamber comprising the cleaning fluid; subjecting the mist to a nonthermal plasma actuator in an outlet tube extending from an opening in a top chamber portion of the substantially closed chamber, wherein the outlet tube comprises a hollow lumen with a distal opening above the top chamber portion for expelling the aerosol droplets to form plasma activated ionic particles; and contacting the article or substantially enclosed space to the plasma activated ionic particles.

Another aspect of the application is directed to a decontamination apparatus comprising: a substantially closed chamber comprising a funnel shaped top chamber portion, a bottom chamber portion, a side chamber portion and an interior chamber portion; an ultrasonic cavitator comprising a proximal end and a distal end, the proximal end being connected to the bottom chamber portion, the distal end extending into chamber interior, the cavitator comprising a piezoelectric transducer to vibrate a material at a resonant frequency, thereby generating a plurality of sheared fluid particles; an inlet tube feeding into the side chamber portion, the tube configured so that a cleaning fluid can passively lie in the bottom chamber portion and submerge the distal end of the ultrasonic cavitator so that the sheared fluid particles flow upward through the cleaning fluid and across the liquid-air interface, forming a mist of aerosol droplets accumulating in the top chamber portion; an outlet tube extending from an opening in the top chamber portion, the outlet tube comprising a hollow lumen with a distal opening above the top chamber portion for expelling the aerosol droplets; and a nonthermal plasma actuator comprising one or more electrodes adjacent to the distal opening, the electrodes configured to generate a high voltage arc activating the aerosol droplets to form plasma activated ionic particles for decontaminating an article, surface, or substantially closed space.

A further aspect of the application is a method for decontaminating an article or substantially enclosed space, comprising the steps of: submerging an ultrasonic cavitator in a reservoir of a cleaning fluid; cavitating the cleaning fluid with ultrasonic vibrations produced by the ultrasonic cavitator; generating a mist comprising aerosol droplets, wherein the mist is generated from the cleaning fluid while the cleaning fluid is being cavitated; subjecting the mist to a nonthermal plasma actuator to form plasma activated ionic particles; and contacting the plasma activated ionic particles to a pathogen.

One other aspect of the application is a method for decontaminating an article or substantially enclosed space, comprising the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to a pathogen.

An additional aspect of the application is an apparatus for decontaminating an article or substantially enclosed space, comprising: a reservoir of cleaning fluid; an ultrasonic cavitator, wherein the ultrasonic cavitator is submerged in the reservoir; a nonthermal plasma actuator, wherein the actuator activates a mist generated from the reservoir; a pathway that connects the nonthermal plasma activator to the reservoir; an outer tube, wherein the outer tube connects the nonthermal actuator to the external atmosphere; and wherein a mist generated from the reservoir can pass through the funnel to the actuator, and further wherein after the mist is activated by the actuator the mist can pass through the outer tube to the external atmosphere.

A further aspect of the application is a method for decontaminating a substantially enclosed space, comprising the steps of: sensing a presence of an airborne or surface pathogen in the atmosphere of a substantially enclosed space using a sensor; communicating the presence of the airborne or surface pathogen from the sensor to a networked computer processor; communicating from the networked computer processor to a decontamination apparatus that an airborne pathogen is present in the substantially enclosed space; activating a decontamination cycle of the decontamination apparatus, wherein the decontamination cycle comprises the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to the airborne pathogen. In certain embodiments, the surface is sampled either manually or via an automated system for non-airborne pathogens.

An additional aspect of the application is a system for decontaminating a substantially enclosed space, comprising: a sensor for airborne or surface pathogens, wherein the sensor is in networked communication with a computer processor; a computer processor, wherein the computer processor is in networked communication with the sensor and a decontamination apparatus; a decontamination apparatus, wherein the decontamination apparatus is in networked communication with the computer processor, and further wherein the decontamination apparatus comprises: a reservoir of cleaning fluid; an ultrasonic cavitator, wherein the ultrasonic cavitator is submerged in the reservoir; a nonthermal plasma actuator, wherein the actuator activates a mist generated from the reservoir; a pathway that connects the nonthermal plasma activator to the reservoir; an outer tube, wherein the outer tube connects the nonthermal actuator to the external atmosphere; and wherein a mist generated from the reservoir can pass through the funnel to the actuator, and further wherein after the mist is activated by the actuator the mist can pass through the outer tube to the external atmosphere.

A still further aspect of the application is a non-transitory computer readable medium providing instructions for repeating decontamination cycles of a decontamination apparatus, the instructions comprising: sensing a presence of a pathogen in a substantially enclosed space; communicating the presence of the pathogen to a computer database; identifying the pathogen sensed in the substantially enclosed space using the computer database; selecting a program of decontamination cycles from the computer database based on the identity of the pathogen; communication the selected program to a decontamination apparatus, wherein the decontamination apparatus is networked to automatically follow the program; performing the decontamination cycles according to the program, wherein each decontamination cycle comprises the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to the airborne pathogen.

A further aspect of the application is a method comprising the step of exposing the substantially enclosed space to a sterilant gas comprising chlorine dioxide, ethylene oxide, ozone, propylene oxide, nitrogen dioxide, formaldehyde or a combination thereof. In some embodiments, the cleaning fluid comprises hydrogen peroxide at a concentration of up to about 9%. In particular embodiments, the cleaning fluid comprises hydrogen peroxide at a concentration of about 7.8%. In some embodiments, the article or substantially closed space is exposed to the plasma activated ionic particles in an amount sufficient to provide greater than 6-$\log^{10}$ reduction of viable bacteria, viable bacterial spores, or viable virus particles relative to untreated controls. In particular embodiments, the article, surface, or substantially closed space is exposed to the plasma activated ionic particles in an amount sufficient to provide greater than 7-$\log^{10}$ killing of bacteria, bacterial spores, or virus particles relative to untreated controls. In other embodiments, the article, surface, or substantially closed space is exposed to the plasma activated ionic particles in an amount sufficient to provide greater than 8-$\log^{10}$ killing of bacteria, bacterial spores, or virus particles relative to untreated controls. In another embodiment, the article, surface, or substantially closed space is exposed to the plasma activated ionic particles in an amount sufficient to provide greater than 9-$\log^{10}$ killing of bacteria, bacterial spores, or virus particles, molds, allergens, parasites, relative to untreated controls.

Another aspect of the application is a decontamination apparatus comprising: a substantially closed chamber comprising a funnel shaped top chamber portion, a bottom chamber portion, a side chamber portion and an interior chamber portion; an ultrasonic cavitator comprising a proximal end and a distal end, the proximal end being connected to the bottom chamber portion, the distal end extending into chamber interior, the cavitator comprising a piezoelectric transducer to vibrate a material at a resonant frequency, thereby generating a plurality of sheared fluid particles; an inlet tube feeding into the side chamber portion, the tube configured so that a cleaning fluid can passively lie in the bottom chamber portion and submerge the distal end of the ultrasonic cavitator so that the sheared fluid particles flow upward through the cleaning fluid and across the liquid-air interface, forming a mist of aerosol droplets accumulating in the top chamber portion; an outlet tube extending from an opening in the top chamber portion, the outlet tube comprising a hollow lumen with a distal opening above the top chamber portion for expelling the aerosol droplets, wherein the size of the hollow lumen is restricted to control the flow of the droplets or a shutter is used to control the flow of the droplets; and a non-thermal plasma actuator comprising one or more electrodes adjacent to the distal opening, the electrodes configured to generate a high voltage arc activating the aerosol droplets to form plasma activated ionic particles for decontaminating an article, surface, or substantially closed space. In certain embodiments, the ultrasonic cavitator is connectively linked to a ultrasonic signal generator. In particular embodiments, the ultrasonic cavitator is configured to generate aerosol droplets between 5 to 5 µm in diameter. One of ordinary skill will understand that the form of plasma science used is not limiting on the invention.

In another embodiment, the distal end of the ultrasonic cavitator comprises a piezoelectric disk, and the piezoelectric transducer is configured to vibrate a surface of the piezoelectric disk as a surface of shearing cleaning fluid. In a further embodiment, the distal end of the ultrasonic cavitator comprises a spray nozzle, and the piezoelectric transducer is configured to vibrate a metallic surface of the nozzle as a surface of shearing cleaning fluid. In certain embodiments, the tube is connected to housing supporting a container comprising a cleaning fluid. In particular embodiments, the resonant frequency is between 25 to 200 kHz. In other embodiments, the spray nozzle produces a focused spray pattern having spray pattern between 0.07 to 1 inch in diameter. In specific embodiments, the spray nozzle produces a conical spray pattern between 2 to 6 inches in diameter. In further embodiments, the spray nozzle produces a fan-shaped spray pattern up to 12 inches wide. In another embodiment, a plurality of ultrasonic spray nozzles are disposed in the interior chamber portion. In other embodiments, the nonthermal plasma actuator comprises a dielectric barrier discharge (DBD), cascaded dielectric barrier discharge, capacitative discharge, gliding arc discharge, resistive barrier discharge, plasma jet, spark discharge, glow discharge or a combination thereof. In a particular embodiment, the non-thermal plasma generator is a volumetric DBD (VDBD) or a surface DBD (SDBD). In particular embodiments, multiple disks, such as multiple piezoelectric wafers, can be used to scale the devices herein.

In certain embodiments, the power source comprises a DC power source, a high frequency AC power source, an RF power source, a microwave power source, a plasma-generating DC power source and a plasma-generating AC power source. In particular embodiments, the cleaning fluid comprises a liquid. In further embodiments, the cleaning fluid comprises hydrogen peroxide, peracetic acid, sodium percarbonate or a combination thereof, and optionally further the cleaning fluid comprises components to increase free radical protection comprising ozone, alkenes, aldehydes, or halogens. In additional embodiments, the chamber is disposed within a larger chamber and is connected to said larger chamber by a tubular wall extending around the non-thermal plasma actuator and structurally configured to allow the plasma activated ionic particles to be expelled into a subchamber in the top of the larger chamber to decontaminate at least one article placed therein. In particular embodiments, the at least one article comprises a medical device or animal tissue material. In certain embodiments, the subchamber further comprises a source of sterilant gas for exposing the at least one article to the sterilant gas. In other embodiments, the sterilant gas comprises chlorine dioxide, ethylene oxide, ozone, propylene oxide, nitrogen dioxide, formaldehyde or a combination thereof. In another embodiments, the subchamber further comprises means for subjecting the at least one article to ultraviolet light. In certain embodiments, decontamination occurs using Hydroxyl Radical Reactive Oxygen Species.

In another embodiment, the housing further comprises a movable cart, wherein the tubular wall, spray nozzle and electrodes extend from an exterior surface of the movable cart. In certain embodiments, the movable cart further comprises means for producing Hydroxyl Radical Reactive Oxygen Species, WFI water or a sterilant gas selected from the group consisting of chlorine dioxide, ethylene oxide, ozone, propylene oxide, nitrogen dioxide, formaldehyde or a combination thereof. In further embodiments, the movable cart further comprises a metal scrubber box, a blower and a carbon activated filter, and the metal scrubber box is structurally configured so that the blower pulls air though the carbon activated filter, and a scrubber is formed by housing, blower and filter working in unison. In certain embodiments, the movable cart further comprises means for contacting the carbon activated filter with ultraviolet light in order to break down plasma activated ionic particles building upon on the filter.

A further aspect of the application is a method for decontaminating an article or substantially enclosed space, comprising the steps of: submerging an ultrasonic cavitator in a reservoir of a cleaning fluid; cavitating the cleaning fluid with ultrasonic vibrations produced by the ultrasonic cavitator; generating a mist comprising aerosol droplets, wherein the mist is generated from the cleaning fluid while the cleaning fluid is being cavitated; subjecting the mist to a nonthermal plasma actuator to form plasma activated ionic particles; and contacting the plasma activated ionic particles to a pathogen. In particular embodiments, the pathogen is a bacteria.

Another aspect of the application is a method for decontaminating an article or substantially enclosed space, comprising the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to a pathogen. In particular embodiments, the force is applied using ultrasonic vibrations. In certain embodiments, the ultrasonic vibrations are produced by an ultrasonic wafer.

Another aspect of the application is an apparatus for decontaminating an article or substantially enclosed space, comprising: a reservoir of cleaning fluid; an ultrasonic cavitator, wherein the ultrasonic cavitator is submerged in the reservoir; a nonthermal plasma actuator, wherein the actuator activates a mist generated from the reservoir; a funnel, wherein the funnel connects the nonthermal plasma activator to the reservoir; an outer tube, wherein the outer tube connects the nonthermal actuator to the external atmosphere; and wherein a mist generated from the reservoir can pass through the funnel to the actuator, and further wherein after the mist is activated by the actuator the mist can pass through the outer tube to the external atmosphere.

A further aspect of the application is a method for decontaminating a substantially enclosed space, comprising the steps of: sensing a presence of an airborne pathogen in the atmosphere of a substantially enclosed space using a sensor; communicating the presence of the airborne pathogen from the sensor to a networked computer processor; communicating from the networked computer processor to a decontamination apparatus that an airborne pathogen is present in the substantially enclosed space; activating a decontamination cycle of the decontamination apparatus, wherein the decontamination cycle comprises the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to the airborne pathogen.

A further aspect of the application is a system for decontaminating a substantially enclosed space, comprising: a sensor for airborne pathogens, wherein the sensor is in networked communication with a computer processor; a computer processor, wherein the computer processor is in networked communication with the sensor and a decontamination apparatus; a decontamination apparatus, wherein the decontamination apparatus is in networked communication with the computer processor, and further wherein the decontamination apparatus comprises: a reservoir of cleaning fluid; an ultrasonic cavitator, wherein the ultrasonic cavitator is submerged in the reservoir; a nonthermal plasma actuator, wherein the actuator activates a mist generated from the reservoir; a funnel, wherein the funnel connects the nonthermal plasma activator to the reservoir; an outer tube, wherein the outer tube connects the nonthermal actuator to the external atmosphere; and wherein a mist generated from the reservoir can pass through the funnel to the actuator, and further wherein after the mist is activated by the actuator the mist can pass through the outer tube to the external atmosphere.

Another aspect of the application is a non-transitory computer readable medium providing instructions for repeating decontamination cycles of a decontamination apparatus, the instructions comprising: sensing a presence of a pathogen in a substantially enclosed space; communicating the presence of the pathogen to a computer database; identifying the pathogen sensed in the substantially enclosed space using the computer database; selecting a program of decontamination cycles from the computer database based on the identity of the pathogen; communication the selected program to a decontamination apparatus, wherein the decontamination apparatus is networked to automatically follow the program; performing the decontamination cycles according to the program, wherein each decontamination cycle comprises the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to the airborne pathogen.

These and other aspects and embodiments of the present application will become better understood with reference to the following detailed description when considered in association with the accompanying drawings and claims.

BRIEF DESCRIPTION OF THE DRAWINGS

FIG. 10A represents a configuration of device elements wherein a cleaning fluid source 40 and a mist generator 42 are linked via an actuating device 70 that has an adjustable range of rotation of up to 360 degrees. FIG. 10B represents a configuration of device elements wherein a cleaning fluid source 40 is interfaced with a mist generator 42 that, in turn, is linked to a mist delivery unit 72 via an actuating device 70 that has an adjustable range of rotation of up to 360 degrees. FIG. 10C represents a configuration of device elements wherein a mist generator 42 is mounted on an actuating device 70 that has an adjustable range of rotation of up to 360 degrees. FIG. 10D represents another configuration of device elements wherein a mist generator 42 feeds into a mist delivery unit 72 that is mounted on an actuating device 70 that has an adjustable range of rotation of up to 360 degrees.

Figure 1:
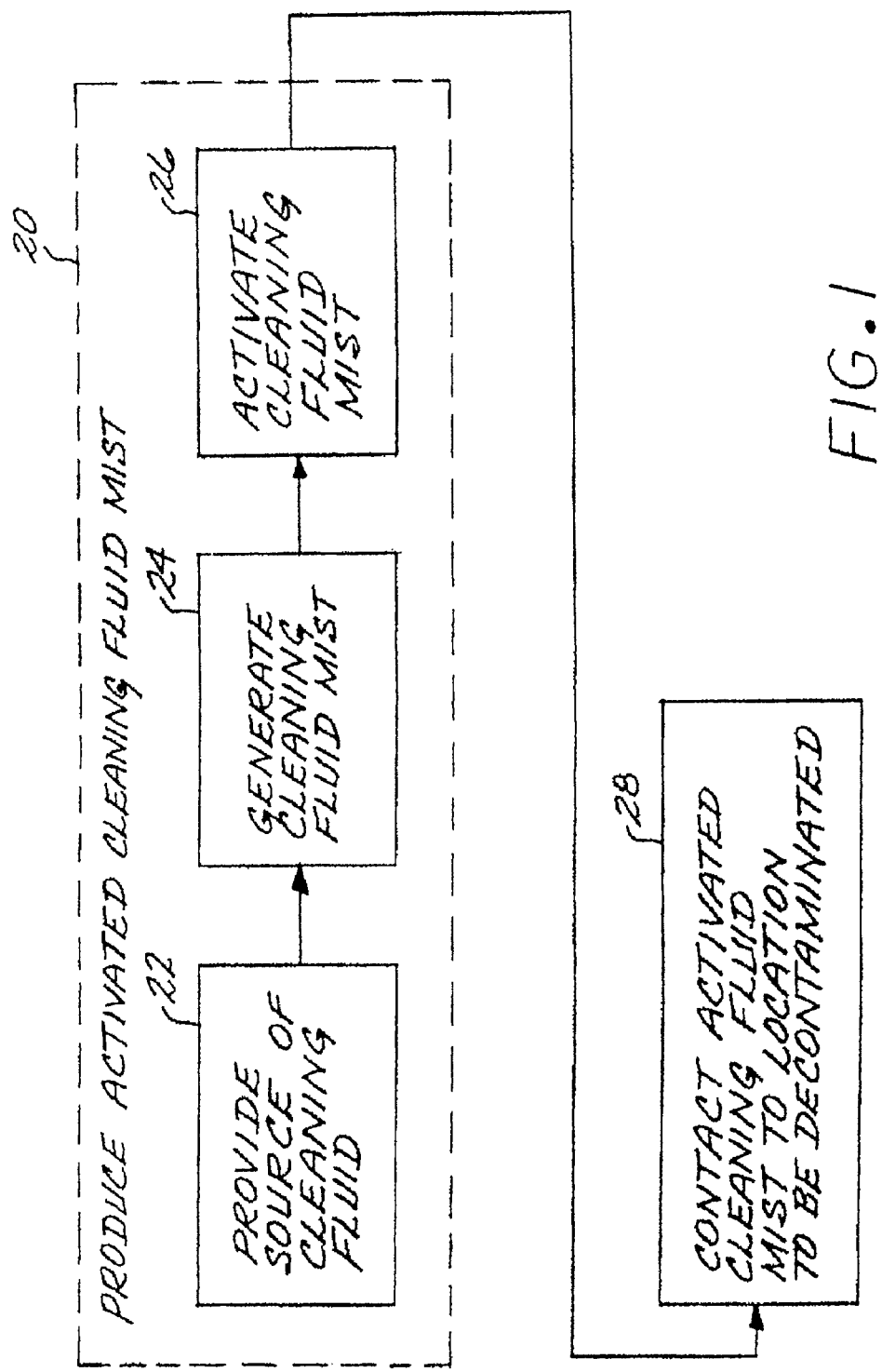
FIG. 1 is a block flow diagram of a general approach for denaturing a biochemical agent using an activated cleaning fluid mist.

Throughout the drawings, the same reference numerals and characters, unless otherwise stated are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and appended claims.

DETAILED DESCRIPTION

Reference will be made in detail to certain aspects and exemplary embodiments of the application, illustrating examples in the accompanying structures and figures. The aspects of the application are described in conjunction with the exemplary embodiments, including methods, materials and examples, such description is non-limiting and the scope of the application is intended to encompass all equivalents, alternatives, and modifications, either generally known, or incorporated here. With respect to the teachings in the present application, any issued patent, pending patent application or patent application publication described in this application is expressly incorporated by reference herein.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

Method and Apparatus for Decontamination Using an Activated Cleaning Fluid Mist

As disclosed in U.S. Pat. No. 6,969,487, which is incorporated herein by reference, a method for performing decontamination comprises the steps of producing an activated cleaning fluid mist wherein at least a portion of the cleaning fluid mist is in an activated state, and contacting the activated cleaning fluid mist to a location to be decontaminated.

FIG. 1 depicts a preferred method for performing decontamination. An activated cleaning fluid mist is produced, numeral 20. Any operable approach may be used, and a preferred approach is illustrated within step 20 of FIG. 1. A source of a cleaning fluid is provided, numeral 22. The cleaning fluid is preferably a liquid that may be vaporized, by any means of force or energy, in ambient-pressure air to form a mist. The liquid cleaning fluid may be stored at one atmosphere or slightly greater pressure, while a cleaning fluid in a gaseous state usually requires pressurized storage. The source of the cleaning fluid may also be a precursor of the cleaning fluid, such as a solid, liquid, or gas that reacts, decomposes, or otherwise produces the cleaning fluid.

A cleaning fluid mist, containing the activatable species and the promoting species, if any, is generated, numeral 24. The mist generator to generate the cleaning fluid mist may be of any operable type. In the preferred case, the cleaning mist or vapor is fine droplets of the vaporized cleaning fluid. In some embodiments, the droplets are preferably roughly uniformly sized, on the order of from about 1 to about 20 micrometers in diameter. In other embodiments, the droplets are preferably roughly uniformly sized, on the order of from about 1 to about 10 micrometers in diameter. In still other embodiments, the droplets are preferably roughly uniformly sized, on the order of from about 1 to about 5 micrometers in diameter. In yet other embodiments, the droplets are preferably roughly uniformly sized, on the order of from about 2 to about 4 micrometers in diameter. Various types of mist generators have been used in prototype studies.

The cleaning fluid mist is activated to produce an activated cleaning fluid mist, numeral 26. The activation produces activated species of the cleaning fluid material in the mist, such as the cleaning fluid material in the ionized, plasma, or free radical states. At least a portion of the activatable species is activated, and in some cases some of the promoting species, if any, is activated. A high yield of activated species is desired to improve the efficiency of the decontamination process, but it is not necessary that all or even a majority of the activatable species achieve the activated state. Any operable activator may be used. The activator field or beam may be electrical or photonic. Examples include an AC electric field, an AC arc, a DC electric field, a DC arc, an electron beam, an ion beam, a microwave beam, a radio frequency beam, and an ultraviolet light beam produced by a laser or other source. The activator causes at least some of the activatable species of the cleaning fluid in the cleaning fluid mist to be excited to the ion, plasma, or free radical state, thereby achieving "activation". These activated species enter redox reactions with the cell walls of the microbiological organisms, thereby destroying the cells or at least preventing their multiplication and growth. In the case of the preferred hydrogen peroxide, at least some of the $H_2O_2$ molecules dissociate to produce hydroxyl ($OH^-$) and monatomic oxygen ($O^-$) ionic activated species. These activated species remain dissociated for a period of time, typically several seconds or longer, during which they attack and destroy the biological microorganisms. The activator is preferably tunable as to the frequency, waveform, amplitude, or other properties of the activation field or beam, so that it may be optimized for achieving a maximum recombination time for action against the biological microorganisms. In the case of hydrogen peroxide, the dissociated activated species recombine to form diatomic oxygen and water, harmless molecules.

Figure 2:
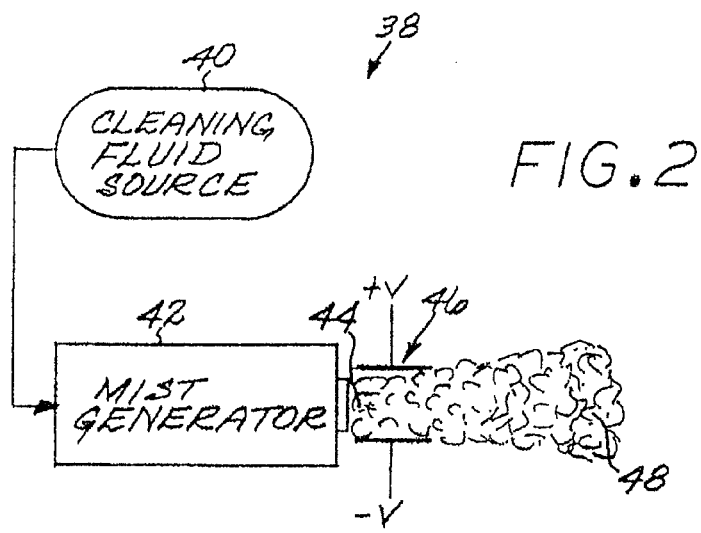
FIG. 2 is a schematic view of a first embodiment of apparatus for denaturing biological agents, with the activator proximally located to the mist generator.
Figure 3:
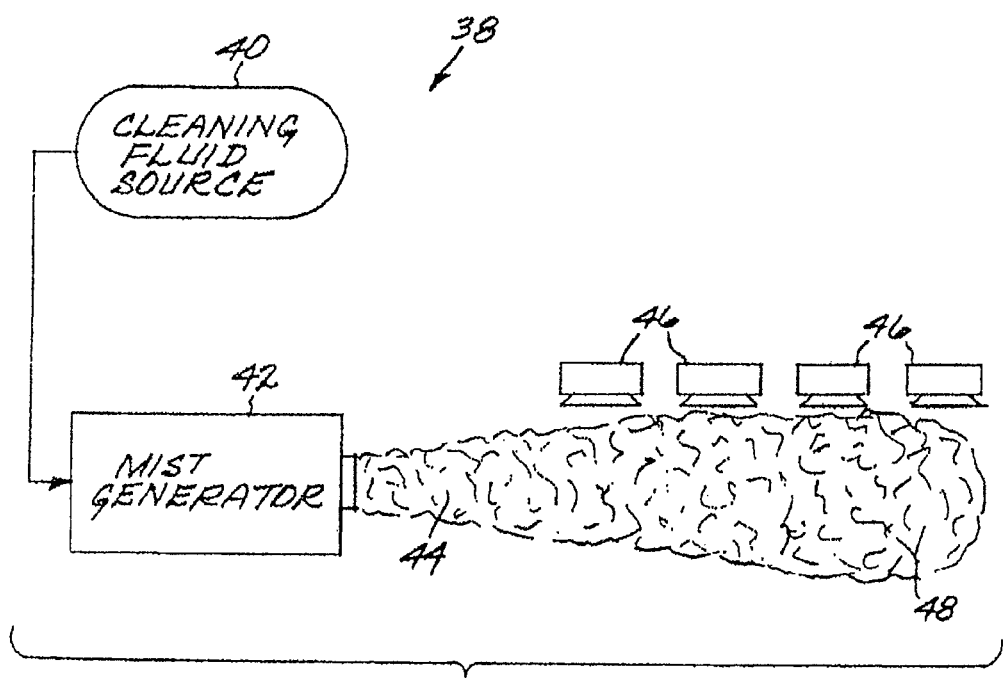
FIG. 3 is a schematic view of a second embodiment of apparatus for denaturing biological agents, with the activator located remotely from the mist generator.
Figure 4:
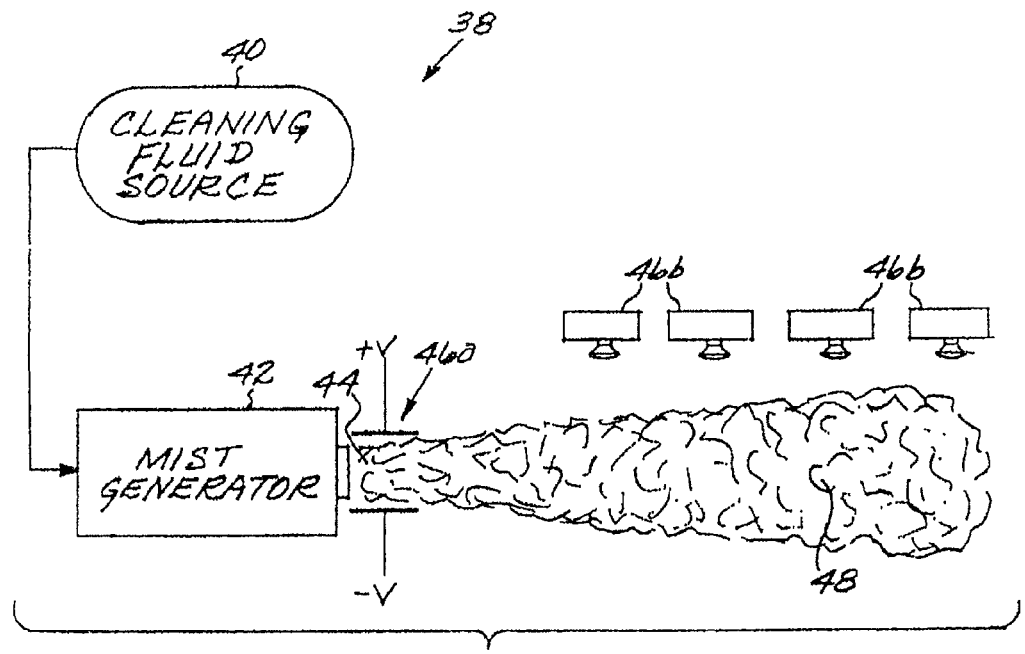
FIG. 4 is a schematic view of a third embodiment of apparatus for denaturing biological agents, with both proximate and remote activators.

The physical relationship of the mist generator and the activator may be of several types, illustrated schematically for three types of decontamination apparatus 38 in FIGS. 2-4. A source of the cleaning fluid 40 provides a flow of the cleaning fluid to a mist generator 42 in each case. The mist generator forms a cleaning fluid mist 44 of the cleaning fluid. The cleaning fluid mist 44 includes the activatable species and the promoting species, if any. In the embodiment of FIG. 2, an activator 46, schematically illustrated as a pair of electrical discharge plates between which the cleaning fluid mist 44 passes, is located proximate to, and preferably immediately adjacent to, the mist generator 42. The mist generator 42 and the activator 46 are typically packaged together for convenience in a single housing in this case. The cleaning fluid mist 44 leaving the mist generator 42 is immediately activated by the activator 46 to produce an activated cleaning fluid mist 48. In the embodiment of FIG. 3, the activator 46, here schematically illustrated as a set of microwave sources, is located remotely from the mist generator 42. The cleaning fluid mist 44 flows from mist generator 42 and remains as a non-activated cleaning fluid mist for a period of time, prior to passing into a region where it is in the influence of and activated by the activator 46. These two embodiments may be combined as shown in FIG. 4, where the cleaning fluid mist 44 is initially activated to form the activated cleaning fluid mist 48 by an activator 46a that is proximate to the mist generator 42, and then kept in the activated state or re-activated as necessary by an activator 46b that is remote from the mist generator 42. In this case, the activator 46b is illustrated to be an ultraviolet light source. The apparatus of FIG. 4 has the advantage that the cleaning fluid is initially activated and then maintained in an activated state for an extended period of time to achieve a prolonged effective state. These various types of apparatus 38 are used in differing situations according to the physical constraints of each situation, and some illustrative situations are discussed subsequently. Particle and/or gas filters may be provided where appropriate to remove particulate matter that is the carrier for microbiological organisms, and also to remove the residual cleaning mist and its reaction products.

The activated cleaning fluid mist 48 is contacted to locations that are to be decontaminated, numeral 28. The types of locations and the manner of contacting lead to a number of specific embodiments of the previously described general approaches, as described next.

Figure 5:
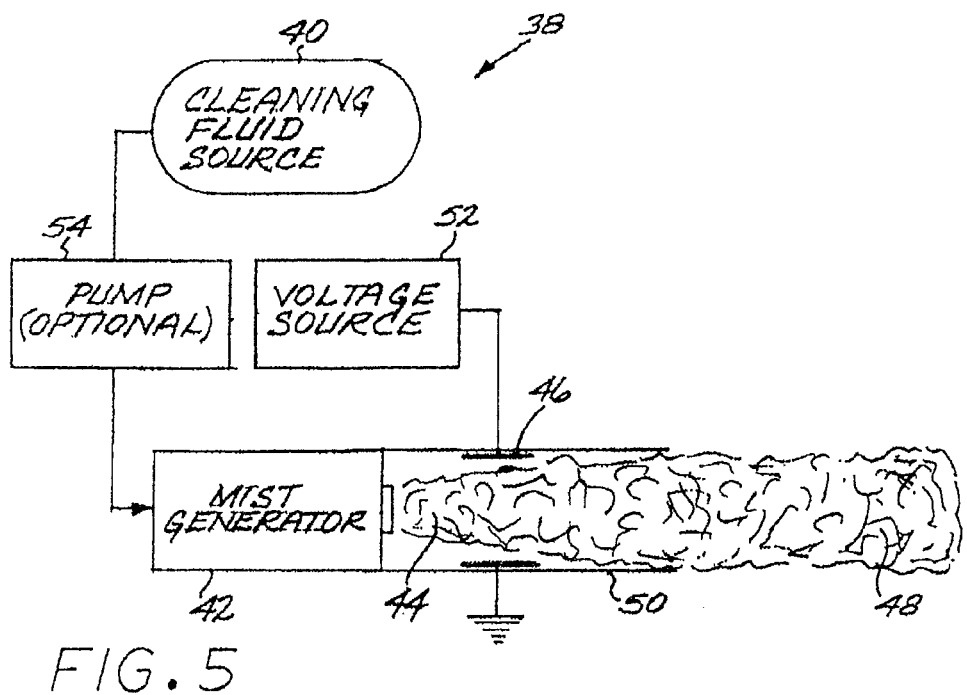
FIG. 5 illustrates a streaming decontamination apparatus.

FIG. 5 illustrates a streaming form of decontamination apparatus 38. This type of apparatus normally uses the general configuration shown in FIG. 2, where the activator 46 is located proximally to the mist generator 42. It does not require an enclosure, although it may be used within an enclosure. In FIG. 5 and other figures illustrating specific embodiments of the apparatus, the common elements of structure will be given the same reference numerals as used elsewhere, and the other description is incorporated into the description of each embodiment. Cleaning fluid from the cleaning fluid source 40 is supplied to the mist generator 42, and the cleaning fluid mist 44 flows from the mist generator 42. The cleaning fluid mist 44 flows through an interior of a tube 50 that channels and directs the flow of the cleaning fluid mist 44. The activator 46 powered by a voltage source 52 activates the cleaning fluid mist 44 as it flows through the interior of the tube 50, so that the activated cleaning fluid mist 48 flows from the tube 50 as a stream. The stream is directed into a volume or against an object that is to be decontaminated.

This basic configuration of FIG. 5 may be scaled over a wide range of sizes. In one example, the cleaning fluid source 40 is a hand-held pressure can of the type commonly used to dispense fluids or gases. The voltage source 52 is a battery and a circuit to supply a high voltage to the activation source 46 for a sufficient period to activate the amount of cleaning fluid that is stored within the pressure can. The tube 50 is the nozzle of the pressure can. In another example, the tube 50 is a hand-held wand operating from a larger-volume cleaning fluid source 40 and with a plug-in or battery electrical voltage source 52. The cleaning fluid source 40 may be pressurized to drive the flow of the cleaning fluid through the tube 50, or there may be provided an optional pump 54 that forces the cleaning fluid through the mist generator 42 and out of the tube 50 with great force.

Figure 6:
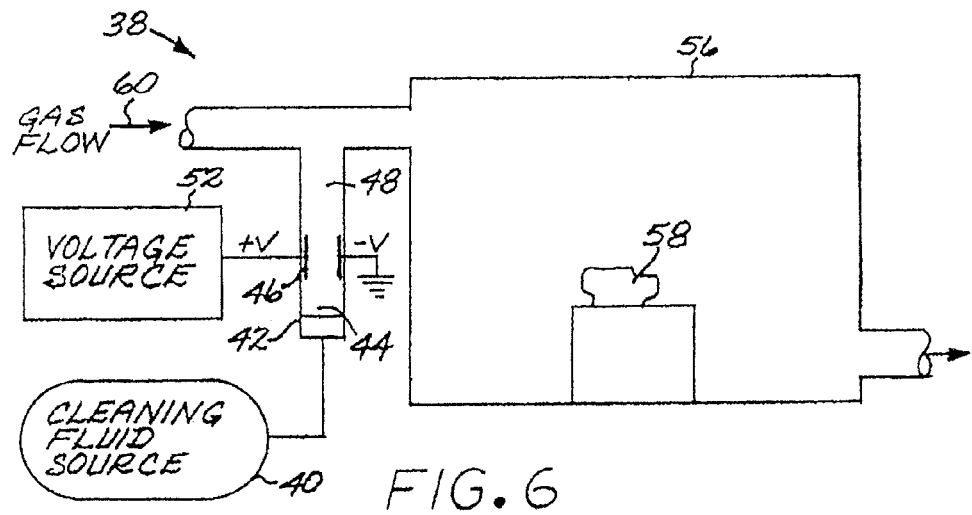
FIG. 6 illustrates a chamber-based decontamination apparatus.

Other forms of the apparatus 38 are primarily used in conjunction with an enclosure, either to enclose the decontamination processing or an object or flow, or to achieve decontamination of the interior of the enclosure. FIG. 6 illustrates the apparatus 38 including an enclosure 56 that serves as a chamber in which an object 58 is decontaminated. The object 58 may be stationary, or it may move through the enclosure 56 on a conveyer. This embodiment also illustrates the form of the present apparatus wherein the activated cleaning fluid mist 48 is added to and mixed with another gas flow 60. The activated cleaning fluid mist 48 mixes with the gas flow 60, and the mixed gas flow contacts the object 58. This embodiment may be implemented either as a continuous-flow system, as illustrated, or as a batch system wherein the enclosure 56 is filled with the activated cleaning fluid mist 48 or with the mixture of the activated cleaning fluid mist 48 and the gas 60 in a batch-wise fashion.

Figure 7:
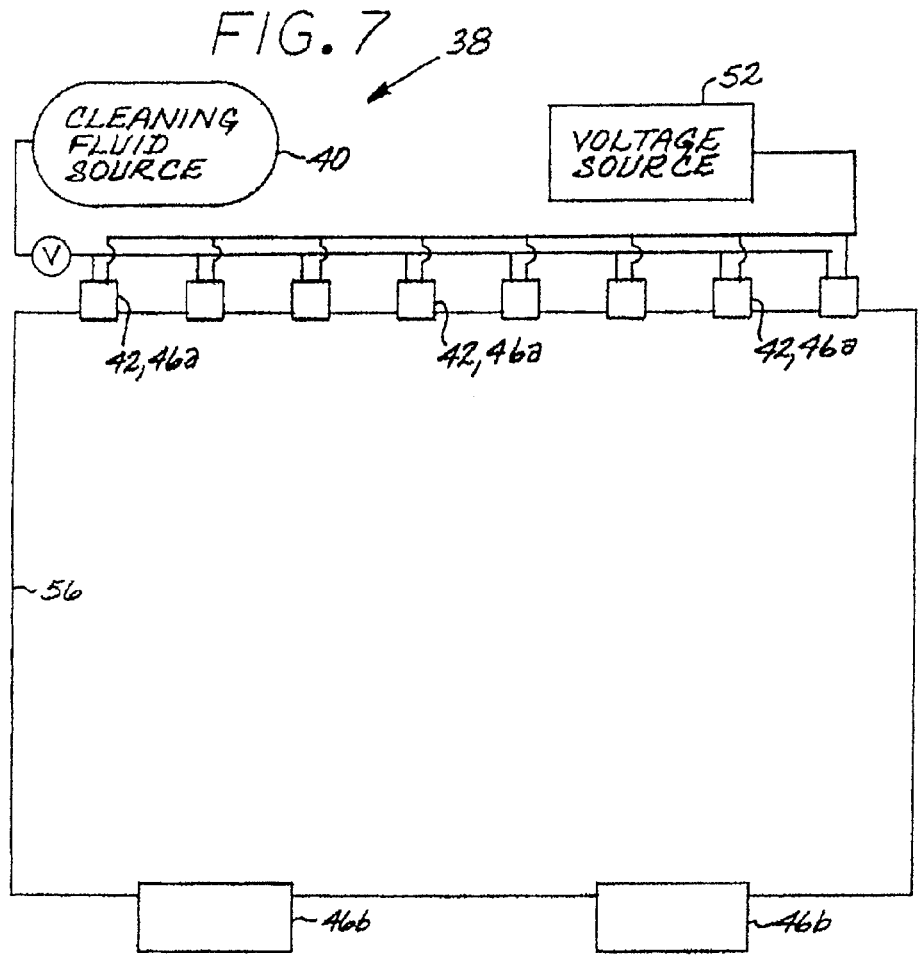
FIG. 7 illustrates a decontamination apparatus for decontaminating a room.

In the embodiment of FIG. 7, the enclosure 56 is formed by the walls, floor, and ceiling of a room or other structure such as a vehicle. The activated cleaning fluid mist is produced by an integrated apparatus of the type illustrated in FIG. 4, in which the mist generator 42 and the activator 46*a* are packaged together as a single unit. An optional second activator 46*b* is provided and used in the manner described in relation to FIG. 4, whose disclosure is incorporated here.

The second activator 46*b* maintains the activated cleaning fluid mist in the activated state for extended periods of time, so as to allow complete decontamination of the room. The second activator 46*b* may be built into the walls, floor, or ceiling of the enclosure 56, or they may be provided as portable units that are positioned within the enclosure 56 only during the decontamination processing. The decontamination apparatus 38 of FIG. 7 decontaminates the interior walls of the room, vehicle, or other structure, as well as objects and people therein. An apparatus 38 of the type shown in FIG. 7 may be used to decontaminate a room (or rooms) in a stationary home, office, or other facility, or the interior of a movable vehicle such as an aircraft, automobile, ship, or military vehicle. The enclosure 56 may also be a protective suit worn by decontamination personnel, to provide continuing decontamination of its interior for normal operation or in the event of a leak in the protective suit.

Figure 8:
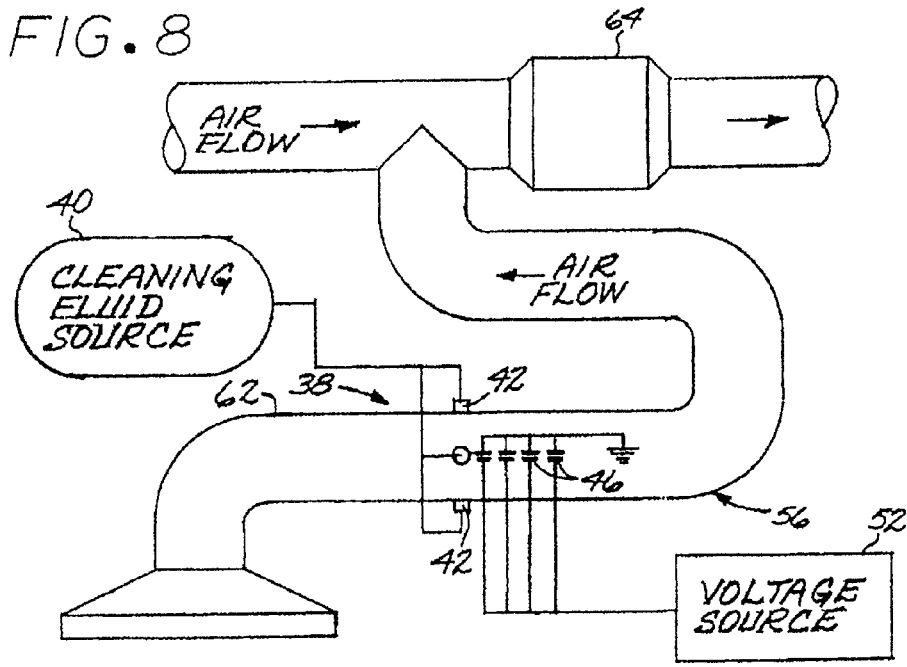
FIG. 8 illustrates a decontamination apparatus for a heating, ventilating, and air conditioning duct system.

FIG. 8 illustrates an embodiment wherein the mist generator 42 and the activator 46 are built into, or temporarily inserted into, an enclosure 56 in the form of a duct of the HVAC system. The duct 62 may be part of the main duct of the HVAC system, or it may be an auxiliary duct added to the HVAC system for receiving the decontamination apparatus 38. A filter 64 is provided downstream of the mist generator 42 and activator 46 for removing particulate and any remaining mist. The filter 64 may be, for example, a porous carbon, low-restriction coalescing filter of the known type.

Figure 9:
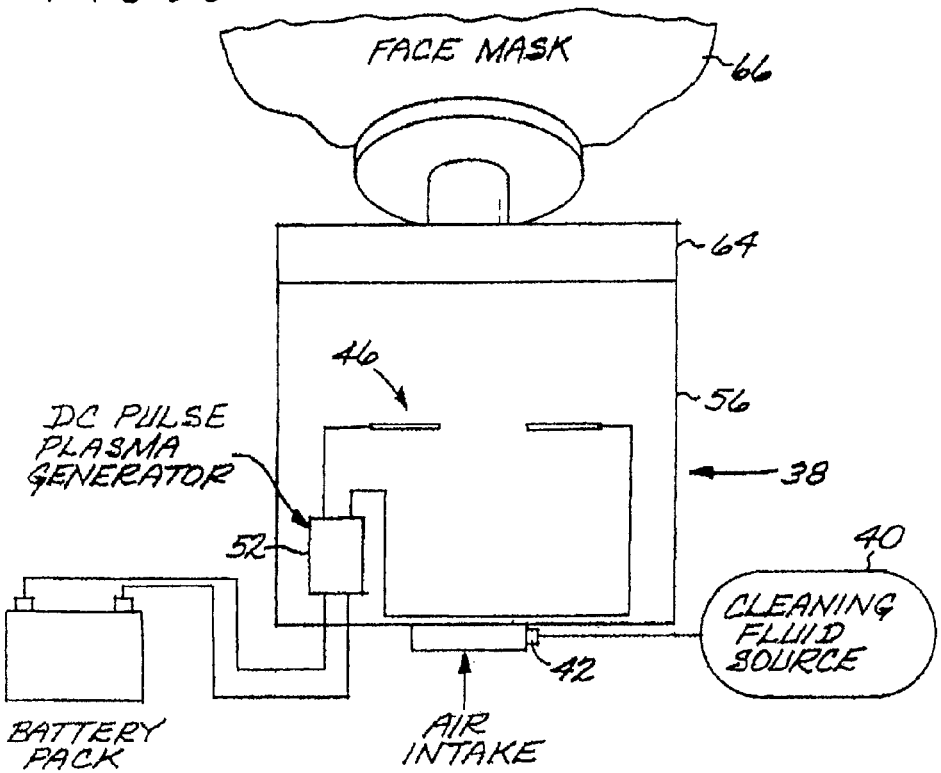
FIG. 9 illustrates a decontamination apparatus for air breathed by a person.

As illustrated by the embodiment of FIG. 8, the decontamination apparatus 38 may be used to decontaminate air and other gas flows, in addition to solid objects. FIG. 9 illustrates an embodiment wherein the decontamination apparatus 38 is used in the manner of a gas mask to furnish decontaminated breathing air for a person. The enclosure 56 is structured as a cannister having an air intake and an outlet providing air to a face mask 66 placed over the face of a person. The cleaning fluid mist is injected into the incoming air by the mist generator 42. The activator 46 may be positioned to activate the cleaning fluid mist in the manner of FIG. 2. Instead, in this case the activator 46 is positioned downstream of the air intake so that the cleaning fluid mist is first thoroughly mixed with the incoming air and thereafter activated by the activator 46. The filter 64 is provided as discussed earlier to remove particulate and any liquid remnants of the mist.

All of these embodiments in FIGS. 2-9 operate in an ambient pressure of about one atmosphere or slightly above one atmosphere, all of which are within the scope of "substantially one atmosphere ambient pressure". As noted earlier, this capability is important because most decontamination situations require the ability to achieve the decontamination without setting up vacuum chambers or pressure chambers. The mist generator produces a small overpressure of the mist as it enters the one atmosphere environment, but does not require either a vacuum or a pressure chamber. Especially in embodiments such as those of FIGS. 3, 4, 6, 8, and 9, particulate matter may be removed from the contaminated region or contaminated gas flow and collected on filters, thereby removing the carrier medium of the microbiological organisms as well as destroying the exposed microbiological organisms themselves.

Decontamination Method

One aspect of the application relates to a method for decontaminating an article or substantially enclosed space, comprising the steps of: shearing a cleaning fluid into a mist comprising aerosol droplets accumulating in a top chamber portion of a substantially closed chamber comprising a funnel shaped top chamber portion, a bottom chamber portion, a side chamber portion and an interior chamber portion, wherein the cleaning fluid is sheared by ultrasonic cavitation; subjecting the mist to a nonthermal plasma actuator to form plasma activated ionic particles; and contacting the article or substantially enclosed space to the plasma activated ionic particles. One of ordinary skill will understand that the form, such as a funnel shaped top chamber, or factor of the aerolized method of applying plasma activated ionic particles is not limiting on the invention.

Another aspect of the application relates to a method for decontaminating an article or substantially enclosed space, comprising the steps of: shearing a cleaning fluid into a mist comprising aerosol droplets by cavitating the cleaning fluid using an ultrasonic cavitator submerged in a substantially closed chamber comprising the cleaning fluid; subjecting the mist to a nonthermal plasma actuator in an outlet tube extending from an opening in a top chamber portion of the substantially closed chamber, wherein the outlet tube comprises a hollow lumen with a distal opening above the top chamber portion for expelling the aerosol droplets to form plasma activated ionic particles; and contacting the article or substantially enclosed space to the plasma activated ionic particles.

A further aspect of the application is a method for decontaminating an article or substantially enclosed space, comprising the steps of: submerging an ultrasonic cavitator in a reservoir of a cleaning fluid; cavitating the cleaning fluid with ultrasonic vibrations produced by the ultrasonic cavitator; generating a mist comprising aerosol droplets, wherein the mist is generated from the cleaning fluid while the cleaning fluid is being cavitated; subjecting the mist to a nonthermal plasma actuator to form plasma activated ionic particles; and contacting the plasma activated ionic particles to a pathogen.

Another aspect of the application relates to a method for decontaminating an article or substantially enclosed space, comprising the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to a pathogen.

As used herein, the term "decontaminating" means acting to neutralize or remove pathogens from an area or article. As used herein, the term "pathogen" includes, but is not limited to, a bacterium, yeast, protozoan, virus, or other pathogenic microorganisms. The term "pathogen" also encompasses targeted bioterror agents.

As used herein, the term "bacteria" shall mean members of a large group of unicellular microorganisms that have cell walls but lack organelles and an organized nucleus. Synonyms for bacteria may include the terms "microorganisms", "microbes", "germs", "bacilli", and "prokaryotes." Exemplary bacteria include, but are not limited to Mycobacterium species, including *M. tuberculosis; Staphylococcus* species, including *S. epidermidis, S. aureus*, and methicillin-resistant *S. aureus; Streptococcus* species, including *S. pneumoniae, S. pyogenes, S. mutans, S. agalactiae, S. equi, S. canis, S. bovis, S. equinus, S. anginosus, S. sanguis, S. salivarius, S. mitis*; other pathogenic Streptococcal species, including *Enterococcus* species, such as *E. faecalis* and *E. faecium; Haemophilus influenzae, Pseudomonas* species, including *P. aeruginosa, P. pseudomallei*, and *P. mallei; Salmonella* species, including *S. enterocolitis, S. typhimurium, S. enteritidis, S. bongori*, and *S. choleraesuis; Shigella* species, including *S. flexneri, S. sonnei, S. dysenteriae*, and *S. boydii; Brucella* species, including *B. melitensis, B. suis, B. abortus*, and *B. pertussis; Neisseria* species, including *N. meningitidis* and *N. gonorrhoeae; Escherichia coli*, including enterotoxigenic *E. coli* (ETEC); *Vibrio cholerae, Helicobacter pylori, Geobacillus stearothermophilus, Chlamydia trachomatis, Clostridium difficile, Cryptococcus neoformans, Moraxella* species, including *M. catarrhalis, Campylobacter* species, including *C. jejuni; Corynebacterium* species, including *C. diphtheriae, C. ulcerans, C. pseudotuberculosis, C. pseudodiphtheriticum, C. urealyticum, C. hemolyticum, C. equi; Listeria monocytogenes, Nocardia asteroides, Bacteroides* species, *Actinomycetes* species, *Treponema pallidum, Leptospirosa* species, *Klebsiella pneumoniae; Proteus* sp., including *Proteus vulgaris; Serratia* species, *Acinetobacter, Yersinia* species, including *Y. pestis* and *Y. pseudotuberculosis; Francisella tularensis, Enterobacter* species, *Bacteriodes* species, *Legionella* species, *Borrelia burgdorferi*, and the like. As used herein, the term "targeted bioterror agents" includes, but is not limited to, anthrax (*Bacillus antracis*), plague (*Yersinia pestis*), and tularemia (*Franciscella tularensis*).

As used herein, the term "virus" can include, but is not limited to, influenza viruses, herpesviruses, polioviruses, noroviruses, and retroviruses. Examples of viruses include, but are not limited to, human immunodeficiency virus type 1 and type 2 (HIV-1 and HIV-2), human T-cell lymphotropic virus type I and type II (HTLV-I and HTLV-II), hepatitis A virus, hepatitis B virus (HBV), hepatitis C virus (HCV), hepatitis delta virus (HDV), hepatitis E virus (HEV), hepatitis G virus (HGV), parvovirus B19 virus, hepatitis A virus, hepatitis G virus, hepatitis E virus, transfusion transmitted virus (TTV), Epstein-Barr virus, human cytomegalovirus type 1 (HCMV-1), human herpesvirus type 6 (HHV-6), human herpesvirus type 7 (HHV-7), human herpesvirus type 8 (HHV-8), influenza type A viruses, including subtypes H1N1 and H5N1, human metapneumovirus, severe acute respiratory syndrome (SARS) coronavirus, hantavirus, and RNA viruses from Arenaviridae (e.g., Lassa fever virus (LFV)), Pneumoviridae (e.g., human metapneumovirus), Filoviridae (e.g., Ebola virus (EBOV), Marburg virus (MBGV) and Zika virus); Bunyaviridae (e.g., Rift Valley fever virus (RVFV), Crimean-Congo hemorrhagic fever virus (CCHFV), and hantavirus); Flaviviridae (West Nile virus (WNV), Dengue fever virus (DENY), yellow fever virus (YFV), GB virus C (GBV-C; formerly known as hepatitis G virus (HGV)); Rotaviridae (e.g., rotavirus), and combinations thereof In one embodiment, the subject is infected with HIV-1 or HIV-2. As used herein, the term "fungi" shall mean any member of the group of saprophytic and parasitic spore-producing eukaryotic typically filamentous organisms formerly classified as plants that lack chlorophyll and include molds, rusts, mildews, smuts, mushrooms, and yeasts. Exemplary fungi include, but are not limited to, *Aspergillus* species, *Dermatophytes, Blastomyces derinatitidis, Candida* species, including *C. albicans* and *C. krusei; Malassezia* furfur, *Exophiala werneckii, Piedraia hortai, Trichosporon beigelii, Pseudallescheria boydii, Madurella grisea, Histoplasma capsulatum, Sporothrix schenckii, Histoplasma capsulatum, Tinea* species, including *T. versicolor, T. pedis T. unguium, T. cruris, T. capitus, T. corporis, T. barbae; Trichophyton* species, including *T. rubrum, T. interdigitale, T. tonsurans, T. violaceum, T. yaoundei, T. schoenleinii, T. megninii, T. soudanense, T. equinum, T. erinacei*, and *T. verrucosum; Mycoplasma geni-*

*talia; Microsporum* species, including *M. audouini, M. ferrugineum, M. canis, M. nanum, M. distortum, M. gypseum, M. fulvum*, and the like.

As used herein, the term "protozoan" shall mean any member of a diverse group of eukaryotes that are primarily unicellular, existing singly or aggregating into colonies, are usually nonphotosynthetic, and are often classified further into phyla according to their capacity for and means of motility, as by pseudopods, flagella, or cilia. Exemplary protozoans include, but are not limited to *Plasmodium* species, including *P. falciparum, P. vivax, P. ovale*, and *P. malariae; Leishmania* species, including *L. major, L. tropica, L. donovani, L. infantum, L. chagasi, L. mexicana, L. panamensis, L. braziliensis* and *L. guyanensi; Cryptosporidium, Isospora belli, Toxoplasma gondii, Trichomonas vaginalis*, and *Cyclospora* species.

As used herein, the term "article" means any solid item or object that may be susceptible to contamination with pathogens. As used herein, the term "substantially enclosed space" means a room, a tent, a building, or any man-made structure that is substantially enclosed and may be susceptible to contamination with pathogens. The term "substantially enclosed space" is not limited to man-made structures, even though embodiments illustrated herein may be preferably directed to decontamination of such structures As used herein, the term "sensor" can refer to any type of sensor suitable for detecting contamination on an apparatus, a surface, or in a substantially closed space. Examples of sensors include, but are not limited to, photosensors, voltaic sensors, weight sensors, moisture sensors, pressure sensors, or any type of biosensor.

As used herein, the term "shearing" refers to the process of using force to fragment liquid particles into discrete groups that move and flow as energized independent subgroups of sheared particles until the groups of particles transition in fluid phase into a mist. As used herein, the term "mist" means a cloud of aerosol droplets. As used herein, the term "aerosol" is a colloid of fine liquid droplets of about 1 to about 20 micrometers in diameter.

As used herein, the term "cleaning fluid" refers to the source of an active species used to decontaminate an article or substantially enclosed space. The preferred active species is hydroxyl ions, and the preferred source is hydrogen peroxide. The source may instead be a more-complex species that produces hydroxyl ions upon reaction or decomposition. Examples of such more-complex species include peracetic acid ($CH_2COO$—$OH+H_2O$), sodium percarbonate ($2Na_2CO_3+3H_2O_2$), and gluteraldehyde ($CH_8O_2$). The cleaning fluid may further include promoting species that aid the active species in accomplishing its attack upon the biological microorganisms. Examples of such promoting species include ethylenediaminetetraacetate, isopropyl alcohol, enzymes, fatty acids, and acids. The cleaning fluid is of any operable type. The cleaning fluid must contain an activatable species. A preferred cleaning fluid comprises a source of hydroxyl ions ($OH^-$) for subsequent activation. Such a source may be hydrogen peroxide ($H_2O_2$) or a precursor species that produces hydroxyl ions. Other sources of hydroxyl ions may be used as appropriate. Examples of other operable sources of hydroxyl ions include peracetic acid ($CH_2COO$—$OH+H_2O$), sodium percarbonate ($2Na_2CO_3+3H_2O_2$), and gluteraldehyde ($CH_8O_2$). Other activatable species and sources of such other activatable species may also be used. In some embodiments, activated ionic particles are generated by passing Water for Injection (WFI) through the arc, providing greater than 3-$\log^{10}$ killing of bacteria, bacterial spores, or virus particles relative to untreated controls.

The cleaning fluid may also contain promoting species that are not themselves sources of activatable species such as hydroxyl ions, but instead modify the decontamination reactions in some beneficial fashion. Examples include ethylenediaminetetraacetate (EDTA), which binds metal ions and allows the activated species to destroy the cell walls more readily; an alcohol such as isopropyl alcohol, which improves wetting of the mist to the cells; enzymes, which speed up or intensity the redox reaction in which the activated species attacks the cell walls; fatty acids, which act as an ancillary anti-microbial and may combine with free radicals to create residual anti-microbial activity; and acids such as citric acid, lactic acid, or oxalic acid, which speed up or intensity the redox reaction and may act as ancillary anti-microbial species to pH-sensitive organisms. Mixtures of the various activatable species and the various promoting species may be used as well. The cleaning fluids are preferably aqueous solutions, but may be solutions in organics such as alcohol. The cleaning fluid source may be a source of the cleaning fluid itself, or a source of a cleaning fluid precursor that chemically reacts or decomposes to produce the cleaning fluid.

As used herein, the term "a nonthermal plasma actuator" means an actuator that activates the cleaning fluid to an activated condition such as the ionized, plasma, or free radical states which, with the passage of time, returns to the non-activated state (a process termed "recombination"). To accomplish the activation, the activator produces activating energy such as electric energy or photonic energy. The photonic energy may be produced by a laser. Examples of activators include an AC electric field, an AC arc, a DC electric field, a DC arc, an electron beam, an ion beam, a microwave beam, a radio frequency beam, and an ultraviolet light beam. The activator may include a tuner that tunes the amplitude, frequency, wave form, or other characteristic of the activating energy to achieve a desired, usually a maximum, re-combination time of the activated cleaning fluid mist. As used herein, the term "plasma activated ionic particles" means activated $OH^-$ ions.

As used herein, an "enclosed space" refers to any chamber, container or space that can be decontaminated with the system of the present disclosure. Examples of enclosed spaces include, but are not limited to, any chamber used in everyday to highly controlled research projects/spaces, sanitation chambers (such as gynoprobe cabinets), BSC, glovebox, research hoods and clinical spaces.

The present disclosure provides a method of decontaminating an article or substantially enclosed space by ultrasonic cavitation. The present inventors have found that the use of ultrasonic cavitation within the cleaning fluid unexpectedly results in a low pressure, low fluid flow mist that significantly enhances kill performance and the ability to decontaminate tightly enclosed environments once the mist has been activated. The method also advantageously reduces the complexity of the machinery used in decontaminating processes as no air compression is required.

Decontamination Devices

Exemplary decontamination devices/systems of the present disclosure comprise an applicator having a cold plasma arc that splits a hydrogen peroxide-based solution into reactive oxygen species, including hydroxyl radicals, that seek, kill, and render pathogens inactive. The activated particles generated by the applicator kill or inactivate a broad spectrum of pathogens and are safe for sensitive equipment. In general, decontamination devices/systems of the present disclosure allow the effective treatment of an exemplary space measuring 104 m² in about 75 minutes, including application time, contact time, and aeration time. Decontamination devices/systems of the present disclosure are scalable and configurable to be effective in any size or volume of space/room/chamber/container. Exemplary spaces include, but are not limited to, clean rooms, research laboratories, production environments, service & technical areas (HEPA filters), material pass-through rooms, corridors and thoroughfares. The decontamination devices/systems of the present disclosure are applicable to areas from a single space to an entire building. The plasma activated ionic particles generated by the present device or system are non-caustic and silver free. In general, the mist generated by the present device or system moves through an enclosed space or over a surface. Exemplary surfaces that can be decontaminated include, but are not limited to, safety cabinets, general laboratory equipment, isolators, HEPA filters, Vivarium caging, and decommissioned equipment.

Another aspect of the present application relates to miniature decontamination devices that comprise a DCV miniature transformer and/or a DCV miniature compressor to reduce power demand and overall weight and size of the device. In some embodiments, a miniature decontamination device has that may be lunchbox-sized to backpack-sized, and/or has a weight in the range of 10-40 lb. In some embodiments, the miniature decontamination device is placed in a backpack, a lightweight portable case or on a wheeled cart. In certain embodiments, the device comprises a small chamber system that heats the decontaminating solution to cause vaporization before passing through the arc system. In particular embodiments, the device comprises a rechargeable battery operated portable wheeled system (similar in form to an IV stand-type system).

In some embodiments, the DCV miniature transformer has an input DC voltage in the range of 6-36V and generates an output of 12-22.5 kV. In some embodiments, the DCV miniature transformer has an input DC voltage of 24V and generates an output of 17.5 kV.

In some embodiments, the DCV miniature compressor provides a pressure in the range of 10-60 psi and has an input DC voltage in the range of 6-36V. In some embodiments, the DCV miniature compressor provides a pressure in the range of 30-40 psi and has an input DC voltage of 24V.

In some embodiments, the miniature decontamination device further comprises a diode/capacitor rectifier that smooths out arc converting process and increases the converting efficiency in AC.

In some embodiments, the miniature decontamination device further comprises low flow pump with a flow rate in the range of 4-40 ml/min and an operating voltage in the range of 6-36 VDC.

In some embodiments, the miniature decontamination device further contains a control module that allows control (e.g., start and or stop the device) and monitoring of the miniature decontaminating device from a remote device such as a tablet or a phone. In some embodiments, the control module further controls data storage, transfer and printing.

Another aspect of the present application relates to a miniature decontamination device that comprises a miniature transformer and an ultrasonic wafer or ultrasonic nebulizer as a mist generator. In some embodiments, the mist generator comprises a substantially closed sonication chamber that comprises a funnel shaped top chamber portion, a bottom chamber portion, a side chamber portion and an interior chamber portion, wherein the cleaning fluid is sheared by ultrasonic cavitation within the sonication chamber. In some embodiments, the device comprises more than one ultrasonic wafer. In some further embodiments, the device comprises 2, 3, 4, 5, 6, 7,8, 9,or 10 ultrasonic wafers.

Figure 15:
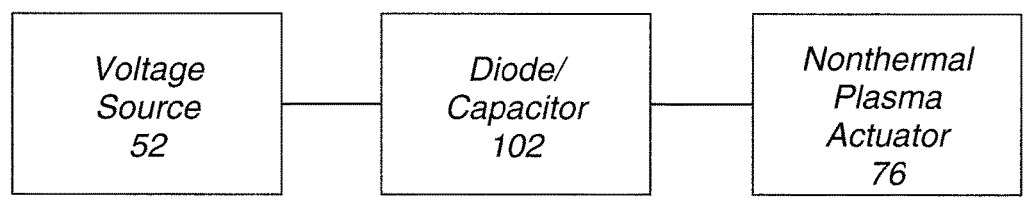
FIG. 15 diagrams an exemplary rectifier for forming free radicals, comprising a voltage source 52, at least one diode/capacitor 102 interfaced with a plasma actuator 76.

Another aspect of the present application relates to a decontamination device that comprises a diode/capacitor rectifier that smooth's out arc converting process and increases the converting efficiency. FIG. 15 diagrams an exemplary rectifier comprising a voltage source 52, at least one diode/capacitor 102 interfaced with a nonthermal plasma actuator 76.

In some embodiments, the decontamination device has a modular structure that reduces the footprint of the device and allows exchange of modules between different devices.

In some embodiments, the decontamination device further comprises low flow pump with a flow rate in the range of 4-40 ml/min and an operating voltage in the range of 6-36 VDC or 10-28 VDC.

In some embodiments, the decontamination device further contains a control module that allows control (e.g., start and or stop the device) and monitoring of the miniature decontaminating device from a remote device such as a tablet or a phone. In some embodiments, the control module further controls data storage, transfer and printing. In some embodiments, the control module allows for remote service and connection, for recording video or data, and for providing feedback to the user during use or after use.

In some embodiments, the decontamination device is mounted on a rotating base that allows better coverage for the area to be decontaminated, as illustrated in the diagrams of FIGS. 10A-D. In some embodiments, the rotating base is a 180-degree rotating base. In some embodiments, the rotating base is a 360-degree rotating base. In some embodiments, the rotating base is an adjustable rotating base having a rotation range of 60-360 degrees. In some embodiments, the rotation is around a single axis. In other embodiments, the rotation is around multiple axes. In still other embodiments, the rotation is in all directions or is a fully spherical motion. FIG. 10A represents a configuration of device elements wherein a cleaning fluid source 40 and a mist generator 42 are linked via an actuating device 70 that has an adjustable range of rotation of up to 360 degrees. FIG. 10B represents a configuration of device elements wherein a cleaning fluid source 40 is interfaced with a mist generator 42 that, in turn, is linked to a mist delivery unit 72 via an actuating device 70 that has an adjustable range of rotation of up to 360 degrees. FIG. 10C represents a configuration of device elements wherein a mist generator 42 is mounted on an actuating device 70 that has an adjustable range of rotation of up to 360 degrees. FIG. 10D represents another configuration of device elements wherein a mist generator 42 feeds into a mist delivery unit 72 that is mounted on an actuating device 70 that has an adjustable range of rotation of up to 360 degrees.

Figure 11A:
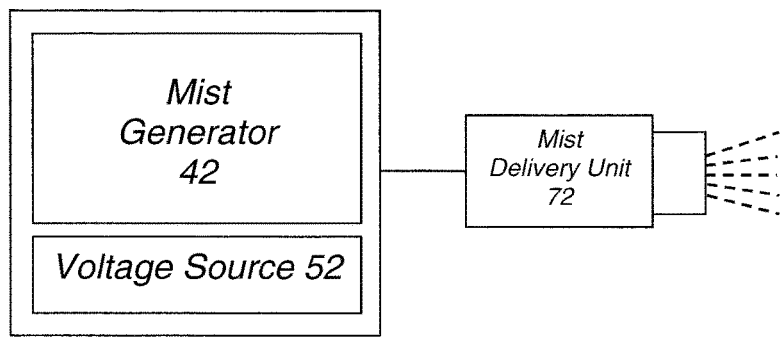
FIG. 11A depicts an embodiment wherein at least a mist generator 42 and a voltage source 52 are contained within a portable housing. The mist generator is functionally connected to a mist delivery unit 72 which may be mounted on the housing or is a remote unit.
Figure 11B:
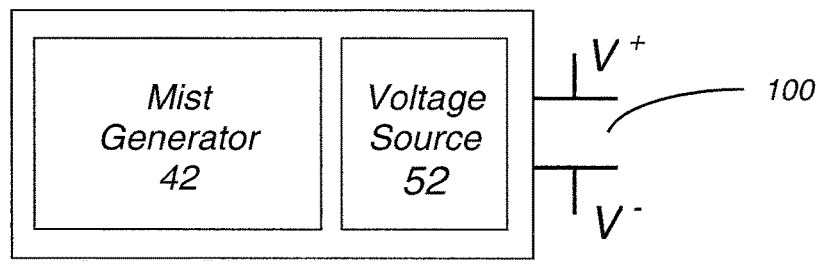
FIG. 11B depicts a mist generator 42 and a voltage source 52 contained within a portable container, wherein the entire unit can be hand held, mounted on another apparatus, or held by/mounted on another machine or a robot.
Figure 11C:
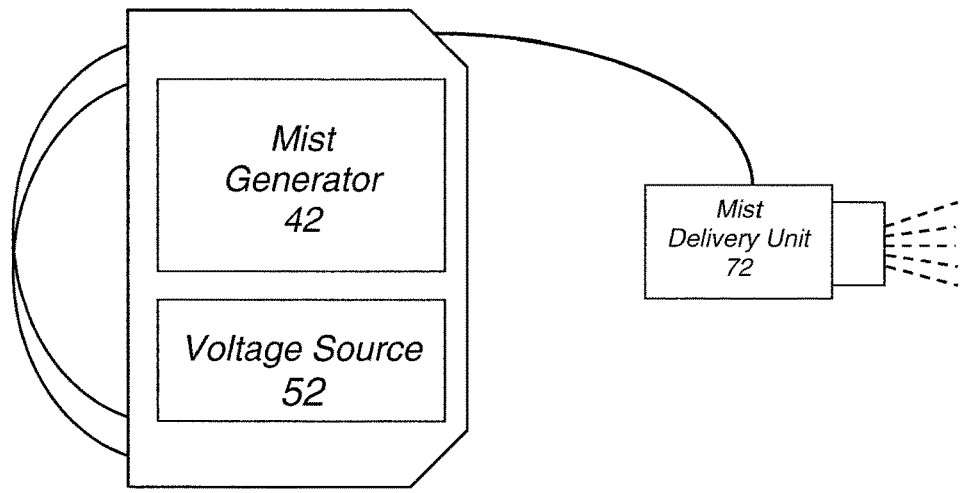
FIG. 11C depicts an exemplary embodiment wherein a mist generator 42 and a voltage source 52 are contained within a wearable container, such as a back pack.
Figure 12A:
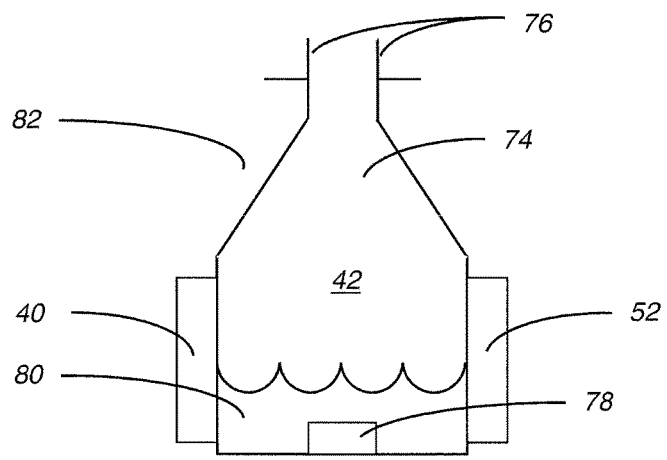
FIG. 12A illustrates the decontamination device comprises an ultrasonic wafer 78 or ultrasonic nebulizer as a mist generator.
Figure 12B:
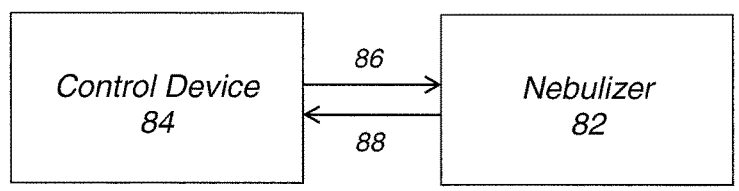
FIG. 12B diagrams a system wherein a mobile/wireless/remote control device 84 is functionally connected to a decontamination device of the present disclosure, such as a nebulizer 82.
Figure 12C:
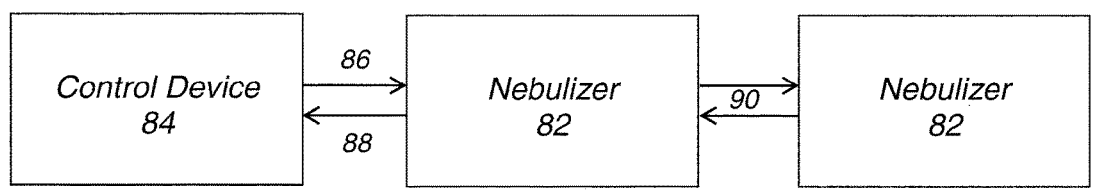
FIG. 12C diagrams an embodiment of the system, wherein the system comprises multiple decontamination devices, such as nebulizers, that are controlled by a control device 84 and further communicate between the nebulizers 82 by wired or wireless means. Information from individual nebulizers 82 can be fed back to the control device 84 either en masse or individually. For example, the dosages emitted by two different nebulizers 82 may start or complete at different times and the data can be reported independently.
Figure 13A:
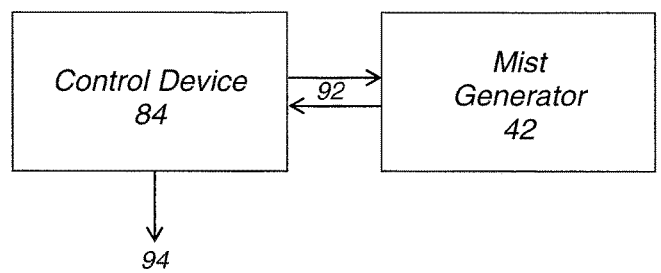
FIGS. 13A-B illustrates a similar system having a single (FIG. 13A) or multiple (FIG. 13B) mist generator(s) 42 being controlled by a control device 84, which further provides data 94 to an external source regarding the treatment of an area or surface.
Figure 13B:
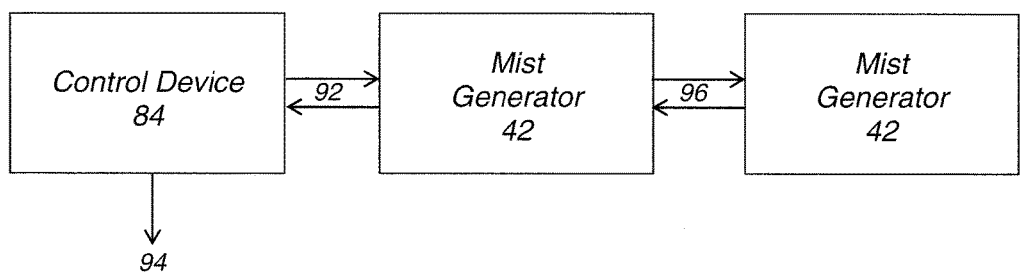
Figure 14:
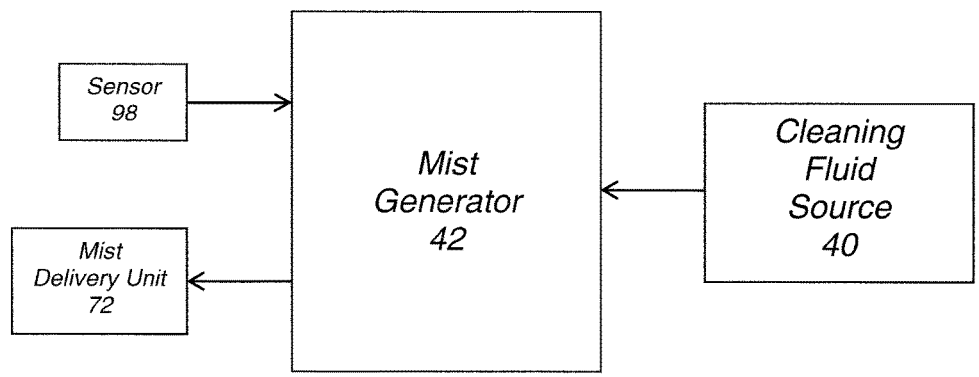
FIG. 14 illustrates a system wherein a mist generator 42, cleaning fluid source 40 and mist delivery unit 72 are further interfaced with a sensor 98.

FIGS. 11A-C depict exemplary embodiments of the decontamination device that are mobile or portable. The depictions are not intended to show the elements of the device in a fixed position within the portable units, rather the placement of individual components as show is merely exemplary and the positions of the elements can be rearranged to suit a particular application. FIG. 11A depicts an embodiment wherein at least a mist generator 42 and a voltage source 52 are contained within a portable housing. In some embodiments, the voltage source 52 is AC. In other embodiments, the voltage source 52 is DC. In still other embodiments, the voltage source 52 can be switched between AC and DC. The mist generator 42 is functionally connected to a mist delivery unit 72 which may be mounted on the housing or is a remote unit. In some embodiments, the mist delivery unit 72 is hand held, mounted on another apparatus, or held by/mounted on another machine or a robot. In some further embodiments, the robots are self-navigating and patrol an area. FIG. 11B depicts a mist generator 42 and a voltage source 52 contained within a portable container, wherein the entire unit can be hand held, mounted on another apparatus, or held by/mounted on another machine or a robot. In some embodiments, the voltage source is AC. In other embodiments, the voltage source 52 is DC. In still other embodiments, the voltage source can be switched between AC and DC. In particular embodiments, the mist is dispersed from the unit via high voltage actuation 100. In some embodiments, the high voltage actuation is persistent. In other embodiments, the high voltage actuation is intermittent. In particular embodiments, the high voltage actuation charges the mist and further atomizes the droplets. FIG. 11C depicts an exemplary embodiment wherein a mist generator 42 and a voltage source 52 are contained within a wearable container, such as a back pack. The mist generator 42 is functionally connected to a mist delivery unit 72 which may be mounted on the container or is a remote unit. In some embodiments, the mist delivery unit 72 is hand held, mounted on another apparatus, or held by/mounted on another machine or a robot.

As exemplified in FIG. 12A, in some embodiments, the decontamination device comprises an ultrasonic wafer or ultrasonic nebulizer 82 as a mist generator. In some embodiments, the mist generator 42 comprises a substantially closed sonication chamber that comprises a bottom chamber portion or reservoir, a top chamber portion 74 forming a pathway between the bottom chamber portion and a plasma actuator 76, a voltage source 52, a side chamber portion comprising a cleaning fluid source 40 and an interior chamber portion, wherein the cleaning fluid 80 that is dispensed into the nebulizer 82 is sheared by ultrasonic cavitation generated by a ultrasonic cavitation device 78 within the sonication chamber. The cleaning fluid 80 is introduced into a fluid chamber or reservoir until it submerges an ultrasonic cavitator 78. The ultrasonic cavitator 78 produces resonant ultrasonic waves that serve to cavitate the cleaning fluid, which produces a mist of aerosol droplets that rise from the fluid through a pathway 74. The mist passes through an applicator head and a plasma actuator, or electrodes 76, where the particles are activated before entering the external atmosphere. In some embodiments a fan may be used to direct the flow of the mist. In certain embodiments, the device comprises a rotating applicator based with a small circulating fan. In other embodiments, the device comprises a self-contained applicator that would include air compressor, fluid pump, and transformer. In some embodiments, heating elements heat the space inside to spread the nebulized mist. In some embodiments, the device comprises rotating heads or nozzles.

The pathway can take any form suitable to direct the aerosol droplets from the reservoir to the plasma actuator 76. In some embodiments, the pathway is in the form of a funnel. In other embodiments, the pathway may be, but is not limited to, in the form of a pipe, tube, elbow or cylinder.

In some embodiments, the plasma actuator is nonthermal. In other embodiments, the plasma actuator is thermal.

FIG. 12B diagrams a system wherein a mobile/wireless/remote control device 84 is functionally connected to a decontamination device of the present disclosure, such as a nebulizer 82. The functional connection can be wired or wireless. In some embodiments, a wireless connection includes, but is not limited to, radio frequency, infrared, wifi, BLUETOOTH, or any other suitable means of wireless communication. In some embodiments, the control device 84 sends control instructions 86 to the nebulizer 82 via the functional connection and the nebulizer 82 send feedback data 88 to the control device 84 via the functional connection. FIG. 12C diagrams an embodiment of the system, wherein the system comprises multiple decontamination devices, such as nebulizers 82, that are controlled by a control device 84 and further two-way communicate 90 between the nebulizers 82 by wired or wireless means. In some embodiments, a system can have a single control unit 84 that controls multiple nebulizers 82 that are situated in different areas of a room, and/or different rooms, and or/attached to, or aimed at, different pieces of equipment, such as a flow hood, that need to be sterilized/decontaminated. One of ordinary skill will understand that the devices may be networked to the control unit individually, or sequentially, or wirelessly, and that the network arrangement depicted herein is not limiting.

FIGS. 13A-B depict a similar system having a single (FIG. 13A) or multiple (FIG. 13B) mist generator(s) 42 which two-way communicate 92, 96, being controlled by a control device 84, which further provides data 94 to an external source regarding the treatment of an area or surface. One of ordinary skill will also understand that the devices may be networked to the control unit individually, or sequentially, or wirelessly, and that the network arrangement depicted herein is not limiting.

FIG. 14 diagrams a system wherein a mist generator 42, cleaning fluid source 40 and mist delivery unit 72 are further interfaced with a sensor 98. In some embodiments, the sensor 98 detects microbes (such as bacteria, parasites, amoebae, or viral particles), that are airborne or contaminating a surface. In some embodiments, the sensor 98, upon detection of contaminants, automatically triggers actuation of the system.

Another aspect of the application is directed to a decontamination apparatus comprising: a substantially closed chamber comprising a funnel shaped top chamber portion, a bottom chamber portion, a side chamber portion and an interior chamber portion; an ultrasonic cavitator comprising a proximal end and a distal end, the proximal end being connected to the bottom chamber portion, the distal end extending into chamber interior, the cavitator comprising a piezoelectric transducer to vibrate a material at a resonant frequency, thereby generating a plurality of sheared fluid particles; an inlet tube feeding into the side chamber portion, the tube configured so that a cleaning fluid can passively lie in the bottom chamber portion and submerge the distal end of the ultrasonic cavitator so that the sheared fluid particles flow upward through the cleaning fluid and across the liquid-air interface, forming a mist of aerosol droplets accumulating in the top chamber portion; an outlet tube extending from an opening in the top chamber portion, the outlet tube comprising a hollow lumen with a distal opening above the top chamber portion for expelling the aerosol droplets; and a nonthermal plasma actuator comprising one or more electrodes adjacent to the distal opening, the electrodes configured to generate a high voltage arc activating the aerosol droplets to form plasma activated ionic particles for decontaminating an article, surface, or substantially closed space.

As used herein, the term "ultrasonic cavitation" means the use of ultrasonic sound to cavitate a fluid, such as a cleaning fluid. Ultrasonic cavitation can be applied to a fluid by a range of methods and devices known to one of skill in the art, including a high pressure ultrasonic nebulizer, an ultrasonic nozzle, or an ultrasonic wafer. As used herein, the term "ultrasonic" means frequencies of sound above the audible range, including anything over 20kHz.

As used herein, the term "ultrasonic cavitator" means a device used to perform ultrasonic cavitation on a cleaning fluid. Examples of an ultrasonic cavitator include a high pressure ultrasonic nebulizer, an ultrasonic nozzle, or an ultrasonic wafer. For example, a high pressure ultrasonic nebulizer atomizes liquid particles at a pressure of 50 to 400 bar to produce aerosol droplets. An ultrasonic nozzle is a spray nozzle that uses high frequency vibration produced by piezoelectric transducers to cavitate a liquid. A preferred embodiment uses an ultrasonic wafer. In one embodiment the ultrasonic wafer is a ceramic diaphragm vibrating at an ultrasonic frequency to create water droplets. In another embodiment, the ultrasonic wafer is a small metal plate that vibrates at high frequency to cavitate a liquid. One of ordinary skill will understand that the choice of ultrasonic cavitator is not limiting on the scope of this application.

Some examples of embodiments using the decontamination apparatus, system, or method of the present disclosure include shipping containers. For example, a shipping container may be equipped with a decontamination system that can sense pathogen load within, or on surfaces of, the container. Exemplary systems can feed information about pathogen load to parties equipped to receive data. In some embodiments, a system can print or record data.

Other examples of embodiments using the decontamination apparatus, system, or method of the present disclosure include import, export, travel quarantine areas or checkpoints. In some embodiments, the system includes a walk-through space or tunnel, conveyer system, moving walkway or any other suitable means for moving persons or objects through the mist generated by the decontamination system.

Still other examples of embodiments using the decontamination apparatus, system, or method of the present disclosure include a vehicle. In some embodiments, the vehicle is a car, truck, bus, train, airplane, or any other form of transportation purposed for the movement of goods or passengers. In further embodiments, the vehicle is an autonomous vehicle.

Yet other examples of embodiments using the decontamination apparatus, system, or method of the present disclosure include space travel, space quarantine, or structures that do not reside on the planet earth.

Some examples of embodiments using the decontamination apparatus, system, or method of the present disclosure include food processing/preparation systems. In some embodiments, the system includes sensors, such as photo-detectors, to activate the apparatus. In some embodiments, the system includes sensors for detecting pathogen load.

Still other examples of embodiments using the decontamination apparatus, system, or method of the present disclosure include self-guiding robots. For example, a self-guiding robot equipped with the decontamination system can move around a space or facility, detect contamination via a single or multiple sensors of the same or different types. A self-guiding robot equipped with the decontamination system can treat a contaminated surface or space until bioload is reduced.

Yet other examples of embodiments using the decontamination apparatus, system, or method of the present disclosure include emergency biocontamination rapid deployment chambers.

Other examples of embodiments using the decontamination apparatus, system, or method of the present disclosure include farms, ranches, livestock facilities or abattoirs. As non-limiting examples, a decontamination apparatus or system can be installed in a poultry facility, such as chicken coops, or a dairy collection facility.

Still other examples of embodiments using the decontamination apparatus, system, or method of the present disclosure include, but are not limited to, gyms, studios, training facilities, or bathrooms.

Other examples of embodiments using the decontamination apparatus, system, or method of the present disclosure include buildings with a decontamination system integrated into the building systems in order to decontaminate the entire building or specific area of the building. In some embodiments, the system is integrated into new construction. In other embodiments, the system is integrated into the automation or ventilation systems of an existing building. In some embodiments, a decontamination system or apparatus of the present disclosure is programmable or automated.

Method for Decontaminating a Substantially Enclosed Space of an Airborne Pathogen A further aspect of the application is a method for decontaminating a substantially enclosed space, comprising the steps of: sensing a presence of an airborne pathogen in the atmosphere of a substantially enclosed space using a sensor; communicating the presence of the airborne pathogen from the sensor to a networked computer processor; communicating from the networked computer processor to a decontamination apparatus that an airborne pathogen is present in the substantially enclosed space; activating a decontamination cycle of the decontamination apparatus, wherein the decontamination cycle comprises the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to the airborne pathogen.

A System for Decontaminating a Substantially Enclosed Space of an Airborne Pathogen An additional aspect of the application is a system for decontaminating a substantially enclosed space, comprising: a sensor for airborne pathogens, wherein the sensor is in networked communication with a computer processor; a computer processor, wherein the computer processor is in networked communication with the sensor and a decontamination apparatus; a decontamination apparatus, wherein the decontamination apparatus is in networked communication with the computer processor, and further wherein the decontamination apparatus comprises: a reservoir of cleaning fluid; an ultrasonic cavitator, wherein the ultrasonic cavitator is submerged in the reservoir; a nonthermal plasma actuator, wherein the actuator activates a mist generated from the reservoir; a funnel, wherein the funnel connects the nonthermal plasma activator to the reservoir; an outer tube, wherein the outer tube connects the nonthermal actuator to the external atmosphere; and wherein a mist generated from the reservoir can pass through the funnel to the actuator, and further wherein after the mist is activated by the actuator the mist can pass through the outer tube to the external atmosphere.

In an exemplary embodiment, the computer system includes a memory, a processor, and, optionally, a secondary storage device. In some embodiments, the computer system includes a plurality of processors and is configured as a plurality of, e.g., bladed servers, or other known server configurations. In particular embodiments, the computer system also includes an input device, a display device, and an output device. In some embodiments, the memory includes RAM or similar types of memory. In particular embodiments, the memory stores one or more applications for execution by the processor. In some embodiments, the secondary storage device includes a hard disk drive, floppy disk drive, CD-ROM or DVD drive, or other types of non-volatile data storage. In particular embodiments, the processor executes the application(s) that are stored in the memory or the secondary storage, or received from the internet or other network. In some embodiments, processing by the processor may be implemented in software, such as software modules, for execution by computers or other machines. These applications preferably include instructions executable to perform the functions and methods described above and illustrated in the Figures herein. The applications preferably provide GUIs through which users may view and interact with the application(s). In other embodiments, the system comprises remote access to control and/or view the system.

A Non-transitory Computer Readable Medium for Decontaminating a Substantially Enclosed Space of a Pathogen A still further aspect of the application is a non-transitory computer readable medium providing instructions for repeating decontamination cycles of a decontamination apparatus, the instructions comprising: sensing a presence of a pathogen in a substantially enclosed space; communicating the presence of the pathogen to a computer database; identifying the pathogen sensed in the substantially enclosed space using the computer database; selecting a program of decontamination cycles from the computer database based on the identity of the pathogen; communication the selected program to a decontamination apparatus, wherein the decontamination apparatus is networked to automatically follow the program; performing the decontamination cycles according to the program, wherein each decontamination cycle comprises the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to the airborne pathogen.

The following examples are by way of illustration only and should not be considered limiting on the aspects or embodiments of the application.

EXAMPLE 1

In a first test series, identical cultures of serratia marcenscens were prepared by plating onto filter papers. One specimen was incubated for 24 hours at 30° C. in air as a control. Significant growth of the bacteria culture was observed. A second specimen was exposed to a 3 percent by volume aqueous hydrogen peroxide mist (which had not been activated) for 60 seconds in air at one atmosphere pressure, and thereafter incubated for 24 hours at 30° C. in air. Significant growth of the bacteria culture was observed. A third specimen was exposed to a 3 percent by volume aqueous hydrogen peroxide mist, which had been activated by passage through a 10.5 kilovolt AC arc, for 60 seconds in air at one atmosphere pressure, and thereafter incubated for 24 hours at 30° C. in air at one atmosphere pressure. This specimen showed no growth of the bacteria culture, which was killed by the treatment. After this demonstration that the activation treatment rendered the 3 percent hydrogen peroxide mist capable of preventing growth, additional respective specimens were tested using 1.5 percent, 0.75 percent, 0.3 percent, and 0 percent ("activated" water vapor only) concentration hydrogen peroxide mists for 60 seconds exposure in air at one atmosphere pressure, and incubated as described. The specimens contacted by the 1.5 percent and 0.75 percent hydrogen peroxide mists showed no growth. The specimen contacted by the 0.3 percent hydrogen peroxide mist showed very slight growth. The specimen contacted by the 0 percent hydrogen peroxide mist showed significant growth of the bacteria culture.

EXAMPLE 2

For a second and third test series, a duct-simulation structure was built. The duct-simulation structure was a pipe about 10 inches in diameter and 10 feet long, oriented vertically. The mist generator and activator were positioned at the top of the pipe, and a fan operating at about 350-400 cubic feet per minute gas flow was positioned at the bottom of the pipe to induce a gas flow downwardly through the pipe. Test ports were located at 1 foot, 2 feet, 4 feet, and 6 feet from the top of the pipe, and specimens to be tested were inserted at the various ports.

In the second test series, bacterial spore strips (each about ¾ inch long and ¼ inch wide) impregnated with about $10^6$ spores per strip of *Bacillus stearothermophilus* were placed in each of the test ports of the duct-simulation structure. After testing, the specimens were incubated at 50° C. for seven days. In the first test specimen series, air only (no hydrogen peroxide) was flowed over the specimens for 15 seconds. Significant growth of the bacteria culture at all test ports was observed after incubation. In the second specimen series, a 6 percent by volume hydrogen peroxide mist was generated, but not activated, and flowed over the specimens for 15 seconds. The same significant growth of the bacteria culture at all test ports was observed as for the first test specimen series. In the third specimen series, this procedure was repeated, but the 6 percent hydrogen peroxide mist was activated by a 15 kilovolt AC arc. No growth of the bacteria culture was observed at any of the test ports. These results for bacillus stearothermophilus are significant, because this bacteria is known to be resistant to growth control using conventional, low percentage non-activated hydrogen peroxide treatments.

EXAMPLE 3

In the third test series, bacterial spore strips like those described above were used, except that the bacteria was *Bacillus subtilis* var. *niger*. *Bacillus subtilis* var. *niger* is a recognized proxy for *Bacillus anthracis*, which is in the same genus and which causes anthrax. Because of its similarity to *Bacillus anthracis*, *Bacillus subtilis* var. *niger* is used in laboratory testing to study growth of anthrax and its control, without the risk of contracting or spreading anthrax. In the first test specimen series, air only (no hydrogen peroxide) was flowed over the specimens for 15 seconds. Significant growth of the bacteria culture was observed after incubation of specimens from all ports. In the second specimen series, a 6 percent by volume hydrogen peroxide mist was generated, but not activated, and flowed over the specimens for 15 seconds. The same significant growth of the bacteria culture was observed at all ports as for the first test specimen series. In the third specimen series, this procedure was repeated, but the 6 percent hydrogen peroxide mist was activated by passage through a 15 kilovolt AC arc. No growth of the bacteria culture was observed at any of the ports. This testing established that this approach controls the growth of the anthrax proxy in the duct simulation structure.

EXAMPLE 4

In further testing, ultrasonic cavitation of the cleaning fluid to generate a low pressure, low air flow mist resulted in superior kill.

A 16×16×16 inch box was built for this testing, with the nozzle of the decontamination apparatus penetrating the bottom of the box in the center of the bottom panel.

6-Log biological (*Geobacillus stearothermophilus*) and chemical (iodine $H_2O_2$) indicators were placed in the center of all of the vertical panels. Biological and chemical indicators were also placed on the bottom panel of the box, immediately next to the nozzle.

Activated mist was injected into the box for one minute and allowed to dwell for five minutes.

The biological indicators were then removed from the box and incubated for 7 days. Following incubation, the biological indicators were examined and exhibited 6 log kill of the bacteria.

Although a particular embodiment of the invention has been described in detail for purposes of illustration, various modifications and enhancements may be made without departing from the spirit and scope of the invention. Accordingly, the invention is not to be limited except as by the appended claims.

EXAMPLE 4

In an efficacy test, the decontamination device/system of the present disclosure was tested against a variety of bacterial spores and gram-negative bacteria (including multiple drug resistant organisms, gram-positive bacteria, mold and viruses. Using procedures described in the present disclosure, the $\log^{10}$ reduction of the organisms in the following table were determined:

| Organism | Classification | Log Reduction |
|---|---|---|
| *Bacillus atrophaeus* (surrogate for *B. anthracic*) | Bacterial spore | >8.3 |
| *Geobacillus stearotherophilus* | Bacterial spore | >6.3 |
| *Bacillus subtilis* | Bacterial spore | >6.0 |
| *Clostridium difficile* | Bacterial spore | >6.0 |
| *Escherichia coli* | Gram Negative | >7.4 |
| *Pseudomonas aeruginosa* | Gram Negative | >6.0 |
| *Serratia marcescens* | Gram Negative | >6.0 |
| *Salmonella entercia* | Gram Negative | >5.5 |
| *Staphylococcus aureus* | Gram Positive | >7.4 |
| Methicillin- resistant *Staphylococcus aureus* | Gram Positive | >5.9 |
| *Bacillus atrophaeus* vegetative cells | Gram Positive | >9.0 |
| *Aspergillus niger* | Mold | >8.0 |
| *Aspergillus* species | Mold | >7.0 |
| *Cladosporium* species | Mold | >7.0 |
| *Penicillium* species | Mold | >7.0 |
| *Stachybotrys chartarum* | Mold | >7.0 |
| *Trichophyton mentagrophytes* | Mold | >6.0 |
| Human rhinovirus 16 (surrogate for human influenza) | Virus | >6.8 |
| Influenza A (H1N1) | Virus | >10 |
| Norovirus | Virus | >6.4 |
| Adenovirus | Virus | >5.8 |

The results presented in the table show that the decontamination device/system of the present disclosure is an effective broad-spectrum surface and air disinfectant/decontaminant. It is effective against, bacterial spores, gram-negative bacteria, gram-positive bacteria, multiple drug resistant organisms, mold and viruses. The decontamination device/system is effective for mold mitigation and remediation, as well as the elimination of bacteria and viruses.

The decontamination cycle discussed herein relates to the conversion of hydrogen peroxide solution to ionized hydrogen peroxide after passing through an atmospheric cold plasma arc. Ionized hydrogen peroxide contains a high concentration of reactive oxygen species composed mostly of hydroxyl radicals. Reactive oxygen species damage pathogenic organisms through oxidation of proteins, carbohydrates, and lipids. This leads to cellular disruptions and/or dysfunction and allows for disinfection/decontamination in targeted areas, including large spaces.

In certain embodiments for direct application onto surfaces, the particle size for the ionized hydrogen peroxide is 2-4 microns, flow rate is 50 ml per minute, dose application is 1 ml per square foot, with an application time of 5 seconds over per square foot of treatment area, and a contact time of 7 minutes to disinfect/decontaminate high touch surfaces. In particular embodiments, the solution used is formulated as silver, chlorine and peracetic acid free, which maximizes material compatibility on rubber, metals, and other surfaces. In other embodiments, effective whole room treatment can be achieved in under 45 minutes for a room which is over 3500 cubic feet. In such embodiments, flow rate may be 25 ml per minute per applicator use 3*d* (which depends on room size), dose application is 0.5 ml per cubic foot. The room is safe to enter once hydrogen peroxide is below 0.2 ppm. Treatment time, dosage, dwell time, etc, can be varied to suit the desired decontamination goals of the user.

In further embodiments, a decontamination system can interface with a building HVAC system for room isolation and aeration. The decontamination system uses automated equipment for decontamination of any closed area with downloadable disinfection/decontamination run data and real-time measurement of injection rates to ensure targeted injection volume. The decontamination system can encompass multiple rooms and customized specifications as required according to room size and usage. In another embodiment, the decontamination system is contained in a handheld device for use in a life science facility. The device is designed to be used by technicians using a trigger on the device to control its use according to the trigger position.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A system for decontaminating a substantially enclosed space, comprising:

a sensor for airborne pathogens, wherein the sensor is in networked communication with a computer processor;

wherein the computer processor is in networked communication with the sensor and a decontamination apparatus;

wherein the decontamination apparatus is in networked communication with the computer processor, and further wherein the decontamination apparatus comprises:

a side chamber;

a reservoir of cleaning fluid, wherein the cleaning fluid comprises a source of an active species for decontamination of a substantially enclosed space, wherein the active species is hydroxyl ions and wherein the source is hydrogen peroxide and the cleaning fluid is silver-free, chlorine-free and peracetic-acid free;

an ultrasonic cavitator comprising a proximal end and a distal end, wherein the ultrasonic cavitator is submerged in the reservoir;

a nonthermal plasma actuator, wherein the actuator activates a mist comprising aerosol droplets generated from the reservoir at substantially one atmosphere ambient pressure;

a funnel, wherein the funnel connects the nonthermal plasma actuator to the reservoir;

an outer tube, wherein the outer tube connects the nonthermal actuator to the external atmosphere; and wherein a mist generated from the reservoir can pass through the funnel to the actuator, and further wherein after the mist is activated by the actuator to form plasma activated ionic particles carried by the aerosol droplets of the mist, wherein the plasma activated ionic particles are hydroxyl ions, the mist is dispersed through the outer tube to the external atmosphere.

2. The system of claim 1, wherein the nonthermal plasma actuator comprises a dielectric barrier discharge (DBD), cascaded dielectric barrier discharge, capacitative discharge, gliding arc discharge, resistive barrier discharge, plasma jet, pulsed spark discharge, glow discharge or a combination thereof.

3. The system of claim 1, wherein the non-thermal plasma generator is a volumetric DBD (VDBD) or a surface DBD (SDBD).

4. The system of claim 1, wherein the ultrasonic cavitator is connectively linked to a ultrasonic signal generator.

5. The system of claim 1, wherein ultrasonic cavitator is configured to generate aerosol droplets between 1 to 5 μm in diameter.

6. The system of claim 1, wherein the distal end of the ultrasonic cavitator comprises a piezoelectric disk, and wherein a piezoelectric transducer is configured to vibrate a surface of the piezoelectric disk as a surface of shearing cleaning fluid.

7. The system of claim 1, wherein the outer tube is connected to a housing comprising the reservoir.

8. The system of claim 7, wherein the housing further comprises a movable cart.

9. The system of claim 8, wherein the movable cart further comprises means for producing a sterilant gas selected from the group consisting of chlorine dioxide, ethylene oxide, ozone, propylene oxide, nitrogen dioxide, formaldehyde or a combination thereof.

10. The system of claim 8, wherein the movable cart further comprises a metal scrubber box, a blower and a carbon activated filter, wherein the metal scrubber box is structurally configured so that the blower pulls air though the carbon activated filter, and wherein a scrubber is formed by housing, blower and filter working in unison.

11. The system of claim 10, wherein the movable cart further comprises means for contacting the carbon activated filter with ultraviolet light in order to break down plasma activated ionic particles building upon on the filter.

\* \* \* \* \*